(12) United States Patent
Ahmed et al.

(10) Patent No.: US 7,867,515 B2
(45) Date of Patent: Jan. 11, 2011

(54) ORALLY DISINTEGRATING SOLID DOSAGE FORMS COMPRISING PROGESTIN AND METHODS OF MAKING AND USE THEREOF

(75) Inventors: Salah U. Ahmed, New City, NY (US); Sundeep Sethia, Suffern, NY (US); Tahseen A. Chowdhury, Washington Township, NJ (US)

(73) Assignee: TEVA Woman's Health, Inc., Woodcliff Lake, NJ (US)

( * ) Notice: Subject to any disclaimer, the term of this patent is extended or adjusted under 35 U.S.C. 154(b) by 0 days.

(21) Appl. No.: 12/003,234

(22) Filed: Dec. 20, 2007

(65) Prior Publication Data

US 2008/0175906 A1 Jul. 24, 2008

Related U.S. Application Data

(60) Provisional application No. 60/875,827, filed on Dec. 20, 2006.

(51) Int. Cl.
*A61K 9/20* (2006.01)
(52) U.S. Cl. ..................... 424/465; 514/170
(58) Field of Classification Search ............... None
See application file for complete search history.

(56) References Cited

U.S. PATENT DOCUMENTS

| | | | |
|---|---|---|---|
| 5,770,227 | A | 6/1998 | Dong et al. |
| 6,086,916 | A | 7/2000 | Agnus et al. |
| 6,156,742 | A | 12/2000 | Mackenzie |
| 6,316,029 | B1 | 11/2001 | Jain et al. |
| 6,368,625 | B1 | 4/2002 | Siebert et al. |
| 6,667,050 | B1 | 12/2003 | Boissonneault et al. |
| 2002/0034540 | A1 * | 3/2002 | Price ............ 424/464 |
| 2005/0013857 | A1 | 1/2005 | Fu et al. |
| 2005/0032755 | A1 | 2/2005 | van Look et al. |
| 2005/0196440 | A1 | 9/2005 | Masters et al. |
| 2005/0288264 | A2 | 12/2005 | Van Look et al. |
| 2006/0275360 | A1 | 12/2006 | Ahmed et al. |
| 2009/0170823 | A1 | 7/2009 | DiLiberti |

FOREIGN PATENT DOCUMENTS

| | | |
|---|---|---|
| CN | 1634077 A | 11/2004 |
| EP | 1161941 A1 | 12/2000 |

OTHER PUBLICATIONS

Task Force on Postovulatory Methods of Fertility Regulation, "Randomised controlled trial of levonorgestrel versus the Yuzpe regimen of combined oral contraceptives for emergency contraception. Task Force on Postovulatory Methods of Fertility Regulation," *Lancet 352*:428-433, Lancet Publishing Group (1998).

von Hertzen, H., et al., "Low dose mifepristone and two regimens of levonorgestrel for emergency contraception: a WHO multicentre randomised trial," *Lancet 360*:1803-1810, Lancet Publishing Group (2002).

International Search Report for International Application No. PCT/US2007/25974, mailed on Sep. 8, 2008, United States Patent Office, Alexandria, Virginia.

Written Opinion for International Application No. PCT/US2007/25974, mailed on Sep. 8, 2008, United States Patent Office, Alexandria, Virginia.

English language abstract of CN 1634077 A (Document FP2).

Plan B® Product Packaging and Information Label, Duramed Pharmaceuticals, Inc., Montvale, New Jersey (Sep. 2006).

\* cited by examiner

*Primary Examiner*—Robert A Wax
*Assistant Examiner*—Bethany Barham
(74) *Attorney, Agent, or Firm*—Sterne, Kessler, Goldstein & Fox P.L.L.C.

(57) ABSTRACT

The present invention is directed to non-effervescent, orally disintegrating solid pharmaceutical dosage forms comprising progestin and methods of making and using the dosage forms to treat conditions in females in need thereof.

29 Claims, 10 Drawing Sheets

ORALLY DISINTEGRATING SOLID DOSAGE FORMS COMPRISING PROGESTIN AND METHODS OF MAKING AND USE THEREOF

This application claims the benefit of the filing date of U.S. Appl. 60/875,827, filed Dec. 20, 2006, the contents of which are hereby incorporated by reference in its entirety.

BACKGROUND OF THE INVENTION

1. Field of the Invention

The present invention is directed to non-effervescent, orally disintegrating solid pharmaceutical dosage forms comprising progestin and methods of making and using the dosage forms to treat conditions in females in need thereof.

2. Background Art

Emergency contraception is generally understood to mean the application of contraceptive measures to a female after an act of sexual intercourse (postcoitus) or undesired insemination, especially after unprotected sexual intercourse. Emergency contraceptive pills (ECPs) and intrauterine devices (IUDs) are the currently available forms of emergency contraception. These methods act both to prevent ovulation or fertilization and possibly post-fertilization implantation of a blastocyst (embryo).

Currently available ECPs, also known as emergency contraceptives (EC), contain higher doses of the same steroidal compounds (estrogens and progestins, or progestins alone) found in regular or conventional daily oral contraceptive pills. The progestin-only method uses levonorgestrel (a synthetic progestogen) in two doses of 0.75 mg 12 hours apart (e.g., Plan B®) or in a single dose of 1.5 mg within 72 hours of coitus. The combined or Yuzpe regimen uses both ethinylestradiol (0.1 mg) and levonorgestrel (0.5 mg) in two doses 12 hours apart within 72 hours of coitus. The mifepristone method uses a large dose of mifepristone, an antiprogestin, either as an ECP or as an abortifacient, depending on whether it is used pre- or post implantation. Emergency contraceptive methods are described in Von Hertzen, H. et al., *Lancet*, 352:428-432 (1988); Ho, P. C. et al., *Human Reproduction*, 8(3):389-392 (1993); U.S. Patent Appl. Pub. No. 2005/0032755; WO 2007/000056; and Von Hertzen, H. et al., *Lancet*, 360:1803-1810 (2002). Additionally, off-label use of high dose(s) of conventional combined or progestin-only oral contraceptive pills are also available for emergency contraception.

Levonorgestrel, a synthetic progestogen, is commonly used in combination with estrogen as a contraceptive and also can be used alone as an emergency contraceptive. Levonorgestrel is also used to treat menstrual disorders, endometriosis and for progesterone replacement therapy.

Pharmaceutical preparations containing levonorgestrel alone and methods of using levonorgestrel alone for emergency contraception are described in U.S. Patent Appl. Pub. No. 2005/0032755. Pharmaceutical preparations containing levonorgestrel alone are described in CN1634077.

Conventional solid dosage forms can be undesirable for treatment of adults who have trouble swallowing such dosage forms. Additionally, a large number of adult patients suffer from dysphagia and have difficulty swallowing such dosage forms. It is also desirable, particularly for emergency contraception, to administer a dosage form having a rapid and consistent onset of action, a high bioavailability, and sustained activity. Rapid onset of action can be achieved by parenteral injection but this is unacceptable to many patients, and can pose challenges outside a clinical setting. Although liquid syrups can be suitable for this purpose, they can be difficult to handle and administer in an accurate dosage. Many active agents are also unstable in liquids over long periods of time. Thus, an orally disintegrating dosage form that disintegrates in the mouth in the absence of water is desirable for its widespread patient acceptance and ease of administration.

BRIEF SUMMARY OF THE INVENTION

The present invention is directed to a non-effervescent, orally disintegrating solid pharmaceutical dosage form comprising (a) a progestin equivalent to about 0.5 mg to about 2.0 mg of levonorgestrel; (b) an ionic disintegrant; and (c) a hydrophilic water-insoluble non-ionic excipient; wherein the ionic disintegrant is present in a concentration of greater than 8% to about 60% by weight of the dosage form and the hydrophilic water-insoluble non-ionic excipient is present in a concentration of about 1% to about 20% by weight of the dosage form.

In some embodiments, the ionic disintegrant is selected from the group consisting of croscarmellose sodium, sodium starch glycolate, polacrilin potassium, carboxymethyl cellulose calcium and combinations thereof. In some embodiments, the ionic disintegrant is in a concentration of about 10% to about 50% by weight of the dosage form.

In some embodiments, the hydrophilic water-insoluble non-ionic excipient is selected from the group consisting of microcrystalline cellulose, pregelatinized starch, cellulose compounds, crospovidone, starches and combinations thereof. In some embodiments, the hydrophilic water-insoluble non-ionic excipient is in a concentration of about 2% to about 15.0% by weight of the dosage form.

In some embodiments, greater than 40% by weight of the progestin dissolves into solution in less than about 7 minutes when the dosage form is placed in a surfactant containing medium according to USP method II at 75 rpm.

In some embodiments, at least 75% by weight of the progestin dissolves into solution in less than about 15 minutes when the dosage form is placed in a surfactant containing medium according to USP method II at 75 rpm.

In some embodiments, at least 75% by weight of the progestin equivalent to about 0.75 mg of levonorgestrel dissolves into solution in less than about 15 minutes when the dosage form is placed in a medium of 5 ppm Tween 80 in 900 mL of water according to USP method II at 75 rpm.

In some embodiments, at least 75% by weight of the progestin equivalent to about 1.5 mg of levonorgestrel dissolves into solution in less than about 15 minutes when the dosage form is placed in a medium of 0.1% SDS in 0.1 N HCl according to USP method II at 75 rpm.

The present invention is also directed to a method of treating a female in need of emergency contraception, the method comprising administering postcoitus to the female a first orally disintegrating solid pharmaceutical dosage form; and administering to the female within about 12 hours of administration of the first dosage form a second orally disintegrating solid pharmaceutical dosage form, wherein each of the first and second dosage forms comprises (a) a progestin equivalent to about 0.75 mg of levonorgestrel; (b) an ionic disintegrant; and (c) a hydrophilic water-insoluble non-ionic excipient; wherein the ionic disintegrant is present in a concentration of greater than 8% to about 60% by weight of the dosage form and the hydrophilic water-insoluble non-ionic excipient is present in a concentration of about 1% to about 20% by weight of the dosage form.

The present invention is also directed to a method of treating a female in need of emergency contraception, the method comprising administering postcoitus to the female an orally disintegrating solid pharmaceutical dosage form comprising: (a) a progestin equivalent to about 1.5 mg of levonorgestrel; (b) an ionic disintegrant; and (c) hydrophilic water-insoluble non-ionic excipient; wherein the ionic disintegrant is present in a concentration of greater than 8% to about 60% by weight of the dosage form and the hydrophilic water-insoluble non-ionic excipient is present in a concentration of about 1% to about 20% by weight of the dosage form.

The present invention is also directed to a therapeutic package for treating a female in need of emergency contraception, the package comprising: (a) one or more non-effervescent, orally disintegrating solid dosage forms of the present invention; (b) a suitable container; and (c) a label directing administering the pharmaceutical solid dosage form to a female in need thereof.

The present invention is also directed to a process for preparing a non-effervescent, orally disintegrating solid pharmaceutical dosage form, the process comprising mixing an ionic disintegrant and a progestin equivalent to about 0.5 mg to about 2 mg of levonorgestrel to form an initial mixture; adding to the initial mixture a hydrophilic water-insoluble non-ionic excipient to form a final mixture; and compressing the final mixture to produce the pharmaceutical dosage form; wherein the ionic disintegrant is present in a concentration of greater than 8% to about 60% by weight of the dosage form and the hydrophilic water-insoluble non-ionic excipient is present in a concentration of about 1% to about 20% by weight of the dosage form.

In some embodiments, the process includes wherein at least 75% by weight of the progestin dissolves into solution in less than about 15 minutes when the dosage form is placed in a surfactant containing medium according to USP method II at 75 rpm. In some embodiments, at least 75% by weight of the progestin equivalent to about 0.75 mg of levonorgestrel dissolves into solution in less than about 15 minutes when the dosage form is placed in a medium of 5 ppm Tween 80 in 900 mL of water according to USP method II at 75 rpm. In some embodiments, at least 75% by weight of the progestin equivalent to about 1.5 mg of levonorgestrel dissolves into solution in less than about 15 minutes when the dosage form is placed in a medium of 0.1% SDS in 0.1 N HCl according to USP method II at 75 rpm. In some embodiments, the process includes wherein greater than 40% by weight of the progestin dissolves into solution in less than about 7 minutes when the dosage form is placed in a surfactant containing medium according to USP method II at 75 rpm. In other embodiments, the process can include adding a non-polymeric water soluble carrier to the initial mixture. In other embodiments, the process can include adding a flavorant, a sweetener or a glidant to the final mixture. In some embodiments, the process can include adding a lubricant to the final mixture.

BRIEF DESCRIPTION OF THE FIGURES

FIG. 3 compares the effect on the dissolution rate of levonorgestrel of the non-ionic disintegrant, crospovidone, NF, with the ionic disintegrants polacrilin potassium and croscarmellose sodium.

FIG. 9 shows the effect of absence of monovalent cations on drug release.

DETAILED DESCRIPTION OF THE INVENTION

Figure 1:
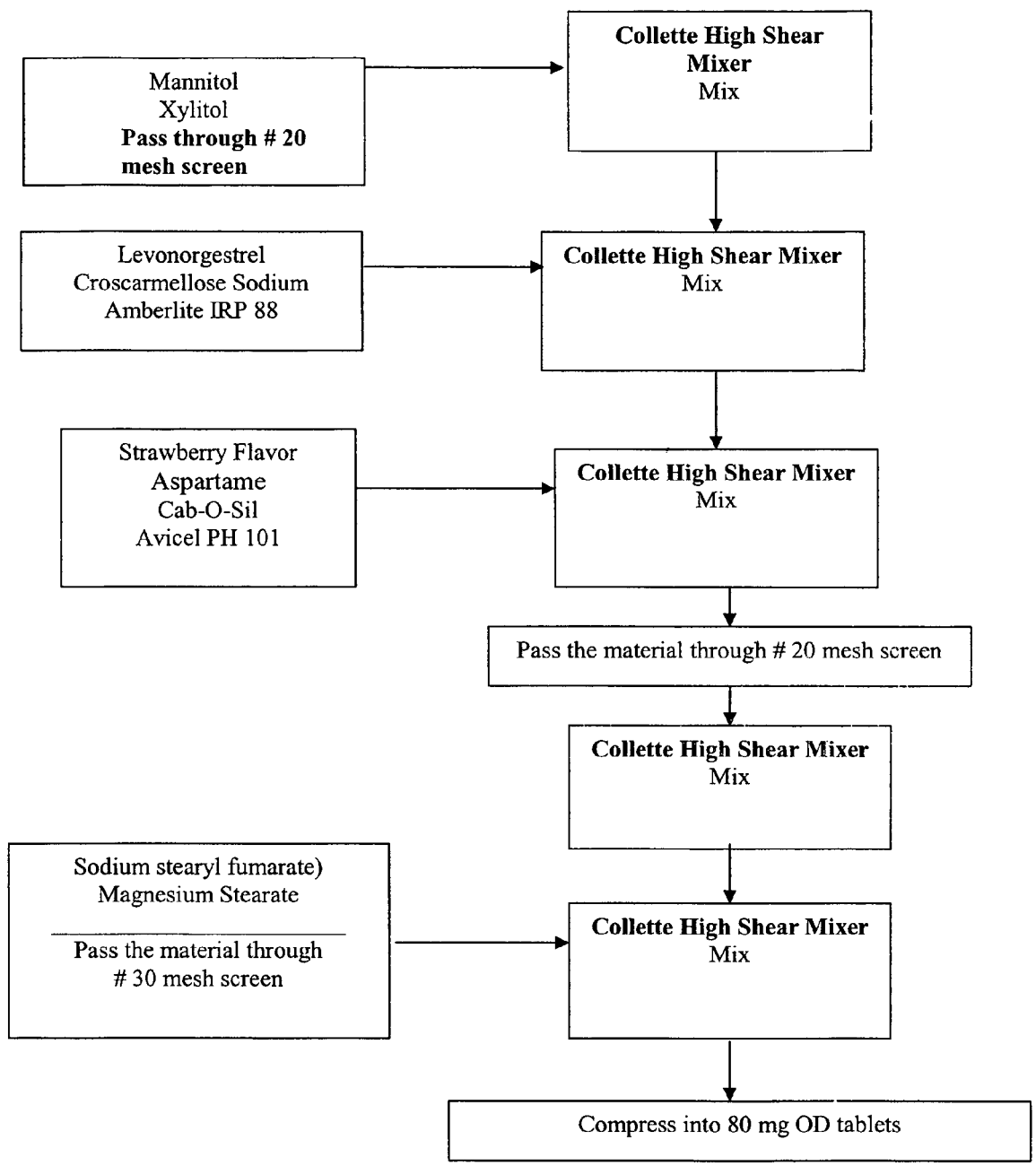
FIG. 1 shows a process flow chart representing a process of preparing the non-effervescent, orally disintegrating solid pharmaceutical dosage form of the present invention.

The present invention is directed to non-effervescent, orally disintegrating solid pharmaceutical dosage forms comprising progestin and a combination of excipients that result in rapid disintegration of the solid dosage forms in the mouth without the need for water intake that can be easily swallowed by a subject in need thereof. The pharmaceutical dosage forms of the present invention provide effective absorption and high bioavailability of progestin, and are particularly useful for treating females in need of emergency contraception.

Non-Effervescent, Orally Disintegrating Solid Pharmaceutical Dosage Forms

The present invention is directed to a non-effervescent, orally disintegrating solid pharmaceutical dosage form comprising (a) a progestin equivalent to about 0.5 mg to about 2.0 mg of levonorgestrel; (b) an ionic disintegrant; and (c) a hydrophilic water-insoluble non-ionic excipient; wherein the ionic disintegrant is present in a concentration of greater than 8% to about 60% by weight of the dosage form and the hydrophilic water-insoluble non-ionic excipient is present in a concentration of about 1% to about 20% by weight of the dosage form.

As used herein, an "orally disintegrating" dosage form refers to solid dosage forms that "disintegrate rapidly, usually within a matter of seconds, when placed upon the tongue." Additionally, "orally disintegrating" can refer to a loss of structural integrity by the dosage forms upon their placement in the buccal cavity of a subject, thereby forming a particulate, viscous, or liquid composition that can be easily swallowed without water. "Disintegrating" also refers to the loss of integrity of the dosage forms of the present invention to form granules, aggregates or particles, as generally described in *Remington: The Science and Practice of Pharmacy*, 21st Ed., Lippincott Williams & Wilkins, Baltimore, Md. (2003), which is incorporated herein by reference in its entirety.

In some embodiments, the dosage forms of the present invention disintegrate in the buccal cavity of a human subject without water intake in about 60 seconds or less, about 45 seconds or less, about 30 seconds or less, about 15 seconds or less, about 10 seconds or less, or about 5 seconds or less. In some embodiments, the pharmaceutical dosage forms of the present invention disintegrate in the buccal cavity of a human subject without water in about 5 seconds to about 60 seconds, about 5 seconds to about 45 seconds, about 5 seconds to about 30 seconds, about 5 seconds to about 15 seconds, about 5 seconds to about 10 seconds, or about 5 seconds to about 8 seconds.

As used herein, "solid pharmaceutical dosage form" refers to a tablet, wafer, film, powder, dragee, or hard or soft gelatin capsule. In some embodiments, the dosage forms of the present invention are tablets. As used herein, the term "tablet" refers to compressed pharmaceutical dosage forms of all shapes and sizes, whether coated or uncoated. The dosage forms are orally disintegrating tablets. The solid dosage forms of the present invention can have a substantially rigid structure, which is mechanically stable and robust. A unit dosage is that amount of the pharmaceutical composition that is individually administered.

The net weight of the pharmaceutical dosage form of the present invention can be about 20 mg to about 1000 mg, about 20 mg to about 500 mg, about 30 mg to about 480 mg, about 30 mg to about 360 mg; about 30 mg to about 240 mg, about 30 mg to about 180 mg, about 30 mg to about 150 mg. In some embodiments, the pharmaceutical dosage forms of the present invention weigh about 30 mg, about 60 mg, about 80 mg, about 100 mg, about 120 mg, about 180 mg, about 240 mg, about 360 mg, or about 480 mg.

As the unit dosage amount of progestin varies, the weight of the pharmaceutical dosage forms can increase or decrease in a proportional manner (i.e., "dose-proportional" dosage forms). In some embodiments, the weight of the pharmaceutical dosage form is constant as the unit dosage amount of progestin varies (i.e., "dose-similar" dosage forms). Dose-similar tablets can be particularly useful because higher doses of progestin can be delivered using small tablets. As used herein, "small tablet" dosage form refers to a dosage form that weighs about 100 mg or less, about 80 mg or less, about 40 mg or less, or about 30 mg or less.

The pharmaceutical dosage forms of the present invention can comprise progestin equivalent to levonorgestrel in a concentration of about 0.05% to about 10%, about 0.05% to about 7.5%, about 0.05% to about 3.0%, about 0.05% to about 2.0%, about 0.07% or about 1.7% by weight of the dosage forms.

Throughout the present disclosure, all expressions of percentage, ratio, corporation, and the like are "by weight" unless otherwise indicated. As used herein, "by weight" is synonymous with the term "by mass," and indicates that a ratio or percentage defined herein is done according to weight rather than volume, thickness, or some other measure.

As used herein, the term "about," when used in conjunction with a percentage or other numerical amount, means plus or minus 10% of that percentage or other numerical amount. For example, the term "about 80%," would encompass 80% plus or minus 8%.

As used herein, "progestin" includes hydrates, solvates, prodrugs, and salts including, but not limited to, acid addition salts such as, for example, hydrochloric, hydrobromic, citric, tartaric, phosphoric, fumaric, malic, and succinic acids, sodium and potassium salts thereof, and combinations thereof. Accordingly, as used herein, the term "levonorgestrel" contemplates all such forms.

The chemical name for levonorgestrel is [18,19-Dinor-pregn-4-en-20-yn-3-one-13-ethyl-17-hydroxy-, (17α)-(-)-], a synthetic progestogen. Levonorgestrel has the following chemical structure:

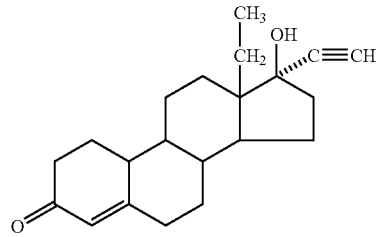

In some embodiments, the levonorgestrel used in the dosage forms of the present invention can be micronized. As used herein, "micronized" means that the particles of the composition have been reduced to particles that are only a few microns or less in diameter. For example, micronized levonorgestrel means that the levonorgestrel particles have been reduced in size such that they are only a few microns or less in diameter.

In some embodiments, the oral dosage forms of the present invention contain a dose of progestin equivalent to about 0.5 mg to about 2 mg of levonorgestrel. In some embodiments, the oral dosage forms of the present invention contain a dose of progestin equivalent to about 0.5 to about 1.5 mg, about 0.5 mg, about 0.75 mg or about 1.5 mg of levonorgestrel.

The dosage values given above are for levonorgestrel, and if a different progestin is employed, an adjustment in the amount based on the relative potency or activity can be made. Correlations in potency among the various progestins are known. See, for example, EP 0 253 607, which is hereby incorporated in its entirety by reference. For example, in a contraceptive regimen, 0.050 mg of levonorgestrel is roughly equivalent to about 0.175 mg of norethindrone acetate, about 0.050 mg of desogestrel, about 0.050 mg 3-ketodesogestrel, about 0.035 mg of gestodene, or about 0.100 mg of norgestrel. It should be understood that when norgestrel is used in place of levonorgestrel, its concentration is twice that of levonorgestrel. Norgestrel (dl-norgestrel) is a racemic mixture of optically active isomers, while levonorgestrel is one of the optically active isomers present in norgestrel.

Equivalent concentrations of progestins can be determined using either in vitro or in vivo assay methods. See, for example, Kuhl, H., *Drugs* 51(2):188-215 (1996); Philibert, D., et al., *Gynecol. Endocrinol.* 13:316-326 (1999); and Lundeen, S., et al., *J. Steroid Biochem. Molec. Biol.* 78:137-143

(2001), in which the relative potencies of various progestins are compared using both in vitro and in vivo test assays. See also, for example, Dickey, R. P., "Contraceptive Therapy," *OBG Management Supplement* (October 2000), pp. 2-6. Each of these documents is hereby incorporated by reference in its entirety.

For example, progestin equivalencies are shown in Table 1.

TABLE 1

Progestin Equivalencies Table

| Progestin | Dose (mg) | Norethindrone Equivalent* Dose (mg) |
|---|---|---|
| Norethynodrel | 9.85 | 9.85 |
|  | 5.00 | 5.00 |
|  | 2.50 | 2.50 |
|  | 2.50 | 2.50 |
| Norethindrone | 10.00 | 10.00 |
|  | 2.00 | 2.00 |
|  | 1.00 | 1.00 |
|  | 1.00 | 1.00 |
| Norethindrone acetate | 1.00 | 1.00 |
|  | 1.00 | 1.00 |
|  | 0.50 | 0.50 |
|  | 0.40 | 0.40 |
| Norethindrone acetate | 2.50 | 2.50 |
|  | 1.00 | 1.00 |
|  | 0.60 | 0.60 |
|  | 1.50 | 1.50 |
|  | 1.00 | 1.00 |
| Ethynodiol diacetate | 1.00 | 1.00 |
| Ethynodiol diacetate | 1.00 | 1.00 |
|  | 1.00 | 1.00 |
| dl-Norgestrel | 0.50 | 0.75 |
|  | 0.30 | 0.45 |
| Levonorgestrel | 0.10 | 0.35 |
|  | 0.15 | 0.52 |

*Equivalencies: 0.10 mg dl-Norgestrel = approximately 0.15 mg Norethindrone

Suitable progestins for use in the present invention include, but are not limited to, natural and synthetic compounds having progestational activity, such as, for example, progesterone, chlormadinone acetate, norethindrone, cyproterone acetate, norethindrone acetate, desogestrel, levonorgestrel, drospirenone, trimegestone, norgestrel, norgestimate, norelgestromin, etonogestrel, gestodene, and other natural and/or synthetic gestagens. Prodrugs of suitable progestins can also be used in a regimen of the present invention.

The expression "prodrug" denotes a derivative of a known direct acting drug, which derivative has enhanced delivery characteristics and therapeutic value as compared to the drug and is transformed into the active drug by an enzymatic or chemical process. Ethynodiol diacetate, which is converted in vivo to norethindrone, is an example of a progestin prodrug that can be used in the present invention. Additional examples of progestin prodrugs include, but are not limited to, norgestimate (which is converted in vivo to 17-deacetyl norgestimate, also known as norelgestromin), desogestrel (which is converted in vivo to 3-keto desogestrel, also known as etonogestrel), and norethindrone acetate (which is converted in vivo to norethindrone).

The pharmaceutical dosage forms of the present invention do not require effervescence to disintegrate in water, but instead rely upon ionic disintegrants to facilitate their disintegration in the buccal cavity.

In some embodiments, the ionic disintegrants are hydrophilic and water-insoluble. Hydrophilic, water-insoluble ionic disintegrants suitable for use with the present invention include, but are not limited to, cross-linked polymers of carboxymethylcellulose sodium (e.g., croscarmellose sodium, available as SOLUTAB®, Blanver Farmoquimica, Ltda., Cotia, Brazil; AC-DI-SOL®, FMC Corp., Philadelphia, Pa.; and VIVASOL®, J. Rettenmaier & Sohne GmbH+Co. KG Ltd., Rosenberg, Germany); cross-linked derivatives of starch (e.g., sodium starch glycolate, available as PRIMOJEL®, Campina Nederland Holding B.V., Zaltbommel, Netherland Antilles; and EXPLOTAB®, Edward Mendell Co., Inc., Carmel, N.Y.); copolymers of methacrylic acid and divinylbenzene (e.g., polacrilex resin, available as AMBERLITE® IRP64, and polacrilin potassium, available as AMBERLITE® IRP88, Rohm and Haas, Philadelphia, Pa.); sulfonated copolymers of styrene and divinylbenzene (e.g., sodium polystyrene sulfonate, available as AMBERLITE® IRP69, and cholestyramine resin, available as DUOLITE® AP143, Rohm and Haas, Philadelphia, Pa.); and combinations thereof.

It has been found that by using a hydrophilic water-insoluble ionic disintegrant (e.g., croscarmellose sodium, sodium starch glycolate, polacrilin potassium) in the dosage form of the present invention, a progestin has a faster and more complete drug release than using a non-ionic disintegrant (e.g., crospovidone), which results in a slower and incomplete drug release.

In some embodiments, an ionic disintegrant is present in the pharmaceutical dosage forms of the present invention in a concentration of greater than 8% to about 60%, about 9% to about 60%, about 9% to about 50%, about 9% to about 40%, about 9% to about 35%, about 9% to about 30%, about 9% to about 25%, about 15% to about 50%, about 15% to about 40%, about 15% to about 35%, about 15% to about 30%, about 20% to about 50%, about 20% to about 45%, about 20% to about 40%, about 20% to about 35%, about 20% to about 30%, about 10%, about 15%, about 19%, about 20%, about 25%, about 27%, or about 30% by weight of the dosage forms.

The pharmaceutical dosage forms of the present invention further comprise a hydrophilic water-insoluble non-ionic excipient. In some embodiments, the hydrophilic water-insoluble non-ionic excipients include a diluent and/or binder. In some embodiments, a hydrophilic water insoluble non-ionic diluent and/or binder can facilitate at least one of compression and/or disintegration of the dosage forms of the present invention. Not being bound by any particular theory, many excipients undergo compaction upon compression, which can frequently decrease the free volume that is normally associated with a mixture, resulting in a compressed composition having a high density and low free volume. Decreasing the free volume and/or porosity of a compressed dosage form typically decreases the rate of disintegration, e.g., in a buccal cavity. Thus, the selection of a diluent and/or binder which retains a high porosity and/or free volume upon compression can help ensure that the dosage forms of the present invention are efficiently penetrated by water and disintegrate rapidly upon administration. Free volume and/or porosity can relate to the density of an excipient, and binders and/or diluents suitable for use with the present invention can therefore be selected based upon their density. In some embodiments, diluents and binders suitable for use with the present invention can have a density of about 0.7 g/cm$^3$ or less, about 0.6 g/cm$^3$ or less, or about 0.5 g/cm$^3$ or less.

Diluents and binders suitable for use with the present invention also include excipients having a fibrous and/or porous structure. In particular, diluents and binders that are both fibrous and porous can be used with the present invention to add to the structural integrity of the solid dosage forms while giving the dosage forms a porous structure.

In some embodiments, hydrophilic water insoluble non-ionic diluents and binders suitable for use with the present invention can be hygroscopic. This can help ensure that water is wicked into the dosage forms to facilitate disintegration. Diluents and binders suitable for use with the present invention include, but are not limited to, water-insoluble celluloses and derivatives thereof (e.g., microcrystalline cellulose and powdered cellulose), water-dispersible celluloses and derivatives thereof (e.g., methylcellulose, hydroxyethylcellulose, hydroxypropyl cellulose, hydroxypropyl methylcellulose, and methylhydroxy ethylcellulose), water-dispersible polymers (e.g., homopolymers of N-vinylpyrrolidone and polyethylene glycol), starch, lactose, sucrose, glucose, dextrose, silicon dioxide, inorganic excipients, and combinations thereof.

In some embodiments, the pharmaceutical dosage forms of the present invention comprise a hydrophilic water insoluble non-ionic diluent and/or a binder in a concentration of about 1% to about 20%, about 1% to about 15%, about 1% to about 10%, about 1% to about 7%, about 3% to about 20%, about 3% to about 15%, about 3% to about 10%, about 3% to about 8%, about 3% to about 7%, about 5% to about 20%, about 5% to about 15%, about 5% to about 10%, about 3%, about 4%, about 5%, about 6%, or about 10% by weight of the dosage forms.

In some embodiments, the hydrophilic water insoluble non-ionic binder or diluent used with the present invention is microcrystalline cellulose. Microcrystalline cellulose is a hydrophilic, water-insoluble excipient that possesses wicking ability, thereby facilitating penetration of water into the dosage forms upon contact, and is commercially available in several grades that range in average particle size from about 20 μm to about 200 μm (e.g., EMCOCEL®, Penwest Pharmaceuticals Co., Patterson, N.J.; and AVICEL®, FMC Corp., Philadelphia, Pa.). Microcrystalline cellulose suitable for use with the present invention can have an apparent density of about 0.28 g/cm$^3$ to about 0.34 g/cm$^3$ and a tap density of about 0.35 g/cm$^3$ to about 0.48 g/cm$^3$. In some embodiments, the pharmaceutical dosage forms of the present invention comprise microcrystalline cellulose in a concentration of about 1% to about 20%, about 1% to about 15%, about 1% to about 10%, about 1% to about 7%, about 3% to about 20%, about 3% to about 15%, about 3% to about 10%, about 3% to about 8%, about 3% to about 7%, about 5% to about 20%, about 5% to about 15%, about 5% to about 10%, about 3%, about 4%, about 5%, about 6%, or about 10% by weight of the dosage forms.

It has been found that high amounts of microcrystalline cellulose in the dosage forms of the present invention appear to decrease the rate and extent of progestin release from the dosage forms into solution.

The dosage forms of the present invention can also comprise one or more pharmaceutically acceptable excipients. As used herein, "pharmaceutically acceptable" refers to those excipients, compounds, materials, and/or compositions that are, within the scope of sound medical judgment, suitable for contact with the tissues of human beings and animals without excessive toxicity, irritation, allergic response, or other possible complications commensurate with a reasonable benefit/risk ratio. In some embodiments, the term "excipient" refers to the substances useful for combining with levonorgestrel to provide a solid dosage form suitable for administering to a subject in need thereof. In addition, one of skill in the art will recognize that pharmaceutically acceptable excipients can be used in the present invention including those listed in *The Handbook of Pharmaceutical Excipients*, 5th Ed., The Pharmaceutical Press and American Pharmacists Association, London, UK and Washington, D.C. (2006) and *Remington: The Science and Practice of Pharmacy*, Lippincott Williams & Wilkins, 21st Ed. (2005), which are incorporated herein by reference in their entirety.

Useful pharmaceutically acceptable excipients include those that impart good flow and compression characteristics to a dry composition that is then compressed. Pharmaceutically acceptable excipients and additives suitable for use with the present invention include, but are not limited to, non-polymeric water-soluble carriers; disintegrants; binders; inorganic excipients; lubricants; glidants; sweeteners; flavorants; and combinations thereof.

In some embodiments, the pharmaceutical dosage forms of the present invention comprise a non-polymeric water-soluble carrier. As used herein, "water-soluble" refers to an excipient having a solubility of at least 1 part in 10 parts of water at 25° C. (i.e., a water solubility of at least 10% by weight). As used herein, "non-polymeric" refers to molecular and oligomeric carriers having a structure comprising about 10 repeat units or less (i.e., carbohydrates comprising 10 or less glycosidic residues). In some embodiments, a non-polymeric water-soluble carrier has a molecular weight of about 500 Daltons or less. In some embodiments, a non-polymeric water-soluble carrier has a heat of solution of about −200 J/g to about 200 J/g. In some embodiments, a non-polymeric water-soluble carrier comprises a non-reducing sugar (i.e., a sugar lacking a glycosidic hydroxyl group or a sugar that is incapable of reacting with a basic nitrogen functional group in a Maillard-type reaction).

Non-polymeric water-soluble carriers suitable for use with the present invention include, but are not limited to, arabinose, dextrose, erythritol, fructose, galactose, inositol, lactitol, maltitol, maltose, mannitol (e.g., PARTECK® M-200, available from Merck KGaA, Darmstadt, Fed. Rep. Germany, and PEARLITOL® SD-200, SD-300 and SD-400, available from Roquette America Inc., Keokuk, Iowa), sorbitol, sucrose, tagatose, trehalose, xylitol (e.g., XYLISORB® 300, available from Roquette America Inc., Keokuk, Iowa), and combinations thereof. As used herein, "inositol" refers to any one of the isomers of inositol, including myo-inositol, the major nutritionally active form of inositol.

A non-polymeric water-soluble carrier is present in the pharmaceutical dosage forms of the present invention in a concentration of about 1% to about 10%, about 3% to about 10%, about 3% to about 7%, about 1% to about 90%, about 20% to about 60%, about 30% to about 60%, about 40% to about 60%, about 20% to about 50%, about 30% to about 50%, about 40% to about 50%, about 42%, or about 46% by weight of the dosage forms.

In some embodiments, the dosage forms of the present invention comprise colloidal silicon dioxide (e.g., CAB-O-SIL®, Cabot Corp., Boston, Mass.; and AEROSIL®, Degussa AG, Frankfurt, Germany). Colloidal silicon dioxide is also known as colloidal silica, fumed silica, light anhydrous silicic acid, silicic anhydride, and silicon dioxide fumed. In some embodiments, colloidal silicon dioxide is present in the pharmaceutical dosage forms of the present invention in a concentration of about 0.1% to about 5%, about 0.1% to about 4%, about 0.1% to about 3%, about 0.2% to about 5%, about 0.2%, to about 2%, about 0.3% to about 1.5%, about 0.5%, about 0.75%, about 1%; about 1.2%, about 1.5%, or about 2% by weight of the dosage forms.

Colloidal silicon dioxide can function as a glidant. As used herein, a "glidant" refers to an excipient that can improve the flow characteristics of a powdered composition. Non-limiting examples of glidants suitable for use with the present invention include various forms of silicon dioxide, talc, and combinations thereof. In some embodiments, a glidant is present in the pharmaceutical dosage forms of the present invention in a concentration of 0.1% to about 5% by weight of the dosage forms.

In some embodiments, the pharmaceutical dosage forms of the present invention further comprise an inorganic excipient. Inorganic excipients suitable for use with the present invention include, but are not limited to, phosphates (e.g., calcium phosphate), sulfates (e.g., calcium sulfate), carbonates (e.g., calcium carbonate), silicates (e.g., aluminum magnesium silicate, aluminum magnesium metasilicate, aluminum silicate, bentonite, silica gel), hydrotalcites, metal hydroxides (e.g., aluminum hydroxide), metal oxides (e.g., titanium dioxide), and combinations thereof. In some embodiments, an inorganic excipient can facilitate the dispersion of the pharmaceutical dosage forms of the present invention. Not being bound by any particular theory, inorganic excipients can facilitate dispersion because they are hygroscopic and can themselves also disintegrate into smaller particles when contacted with water. Thus, when an inorganic excipient is present in the dosage forms of the present invention, a lower concentration of a hydrophilic, water-insoluble ionic disintegrant can be used. For example, an inorganic excipient can replace the hydrophilic, water-insoluble ionic disintegrant in the dosage forms of the present invention in a one-to-one manner up to about 50% by weight of the hydrophilic, water-insoluble disintegrant in the dosage forms. In some embodiments, the concentration of an inorganic excipient in the pharmaceutical dosage forms of the present invention can be determined by the concentration of the hydrophilic, water-insoluble ionic disintegrant in the dosage forms. For example, the ratio of the hydrophilic, water-insoluble ionic disintegrant to inorganic excipient can be about 100:1 to about 1:1, about 50:1 to about 1:1, about 20:1 to about 4:1, or about 10:1 to about 5:1 by weight. In some embodiments, a water-insoluble excipient suitable for use with the present invention comprises a combination of a disintegrant and calcium silicate (RXCIPIENTS® FM1000, J.M. Huber Corp., Edison, N.J.). Various forms of calcium silicate for use with the present invention can include, for example, $CaSiO_3$, $Ca_2SiO_4$, and $Ca_3SiO_5$.

In some embodiments, the dosage forms of the present invention are produced by compression, and can be compressed dosage forms. "Compressed" refers to a mixture or composition that has been compacted under pressure. A compressed composition has a density greater than that of the composition prior to compression. The compressed composition can also have a different shape than the composition prior to compression. The dosage forms of the present invention can be prepared by any method of compression known in the art.

In some embodiments, the concentration of a non-polymeric water-soluble carriers, a hydrophilic, water-insoluble ionic disintegrant, hydrophilic water-insoluble non-ionic excipients such as a diluent, and a binder can be selected to optimize the physical integrity of the dosage forms of the present invention. Not being bound by any particular theory, the durability and robustness of the compressed dosage forms of the present invention can be estimated using the compaction index of the excipients used to prepare the dosage forms. As used herein, "compaction index" refers to the force in kiloponds (kp) required to fracture a solid mass prepared by compaction of 500 mg of powder under 1000 lbs pressure using a $^{16}/_{32}$" die and flat face punches. To obtain dosage forms having low hardness, a mixture used to prepare the dosage forms can have a compaction index of at least about 5 kp/500 mg/1000 lbs. Not being bound by any particular theory, the compaction index can be used as an indicator of particle interactions in a compressed solid dosage form. For example, the compression of a dry mixture usually has a significant effect on the inter-particle interactions within the mixture, and can involve combinations of:

(i) closer contact between particles and the exclusion of air;
(ii) alignment and interlocking of particles;
(iii) the development of stresses and shearing forces that result in fracture and the generation of smaller particles;
(iv) elastic and plastic deformations of particles that can change particle shape; and
(v) chemical bonding between adjacent particles, especially during long-term storage.

In some embodiments, the dosage forms of the present invention further comprise an excipient having a —CHCOOH functional group selected from the group consisting of: tartaric acid, citric acid, malic acid, succinic acid, sodium and potassium salts thereof, and combinations thereof. In some embodiments, an excipient having a —CHCOOH functional group is present in the dosage forms of the present invention in a concentration of about 0.1% to about 5% by weight of the dosage forms.

In some embodiments, the pharmaceutical dosage forms of the present invention further comprise a lubricant. As used herein, a "lubricant" refers to an excipient that can prevent adhesion of a dry composition to a surface (e.g., a surface of a mixing bowl, a compression die and/or punch). A lubricant can also reduce interparticle friction within a substantially homogeneous powder and aid in the ejection of a compressed dosage form from a die cavity after compression. Lubricants suitable for use with the present invention include, but are not limited to, magnesium stearate, calcium stearate, zinc stearate, sodium stearate, stearic acid, aluminum stearate, leucine, glyceryl behenate, sodium lauryl sulfate, sodium stearyl fumarate (e.g., PRUV®, Sohne GmbH & Co., Rosenberg, Germany), hydrogenated vegetable oil, and combinations thereof. In some embodiments, the lubricant is magnesium stearate, sodium stearyl fumarate, or a combination thereof.

In some embodiments, a lubricant is present in the dosage forms of the present invention in a concentration of about 0.1% to about 10%, about 0.1% to about 6%, about 0.1% to about 5%, about 0.1% to about 4%, about 0.1% to about 3%, about 0.1% to about 2%, or less than about 2% by weight. In some embodiments, magnesium stearate is present in the dosage forms of the present invention in a concentration of about 0.1% to about 3%, about 0.2% to about 2%, about 0.3% to about 3%, about 0.3% to about 1.5%, about 0.6%, about 0.7%, about 0.75%, about 0.8%, about 1%, or about 1.5% by weight of the dosage forms. In some embodiments, sodium stearyl fumarate is present in the dosage forms of the present invention in a concentration of about 0.1% to about 10%, about 0.2% to about 5%, about 0.5% to about 3%, about 0.6%, about 0.7%, about 0.75%, about 0.8%, about 1%, about 1.5%, or about 2% by weight of the dosage forms.

In some embodiments, the pharmaceutical dosage forms of the present invention further comprise a sweetener. Sweeteners suitable for use with the present invention have a sweet taste and are soluble in water (e.g., at least 1 part sweetener can be dissolved in about 10 parts water). Non-limiting examples of natural and artificial sweeteners suitable for use with the present invention include saccharin sodium, acesulfame potassium, altitame, aspartame, cyclamic acid and its salts (e.g., sodium cyclamate), dihydrochalcones, erythritol, fructose, glucose, glycerrhizinate, lactose, maltodextrin, mannitol, monellin, neotame, paratinose, rebulose, sorbitol, stevioside, sucralose, sucrose, thaumatin, xylitol, and combinations thereof. In some embodiments, a sweetener for use with the present invention is selected from the group consisting of saccharin, sucralose, aspartame, and combinations thereof.

In some embodiments, the pharmaceutical dosage forms of the present invention are substantially free of sugar (i.e., "sugar-free"). "Sugar-free" can also refer to a pharmaceutical dosage form that is substantially free of complex carbohydrates and/or polysaccharides that can be readily converted to sugars in the oral cavity. A sugar-free pharmaceutical dosage form can offer reduced caloric value, reduced dental caries and other dental hygienic issues, and can be preferable for administering to subjects seeking to control sugar intake (i.e., diabetic subjects). Sugar-free sweeteners suitable for use with the present invention include, but are not limited to, saccharin and salts thereof (e.g., saccharin sodium), acesulfame potassium, altitame, aspartame, cyclamic acid and its salts (e.g., sodium cyclamate), dihydrochalcones, glycerrhizinate, monellin, neotame, saccharin, stevioside, sucralose, thaumatin, sugar alcohols (e.g., mannitol, xylitol, maltitol, isomalt, erythritol, lactitol and sorbitol) and combinations thereof.

In some embodiments, a sweetener is present in the pharmaceutical dosage forms of the present invention in a concentration of 0.0005% to about 10%, 0.0005% to about 10%, about 0.001% to about 10%, about 0.1% to about 10%, or about 0.1% to about 5% by weight of the dosage forms. In some embodiments, the pharmaceutical dosage forms comprises aspartame in a concentration of about 1% to about 10%, about 2% to about 6%, about 2% to about 3%, about 4%, about 5%, or about 6% by weight of the dosage forms.

In some embodiments, the pharmaceutical dosage forms of the present invention further comprise a flavorant. As used herein, a "flavorant" refers to a natural or artificial flavoring that can be added to the pharmaceutical dosage forms to improve their taste, or to mask an unpleasant taste. Flavorants can be combined, as desired, to produce a particular flavor mixture which is compatible with a particular medication. Flavorants suitable for use with the present invention include, but are not limited to, raspberry, strawberry, cherry, almond, citrus fruit, vanilla, vanilla cream, mint, spearmint, wintergreen, grape, coconut, chocolate, menthol, licorice, butterscotch and combinations thereof. Citrus fruit flavorings suitable for use with the present invention include, but are not limited to, orange, tangerine, lemon, lime, lemon-lime, and combinations thereof. A flavorant can be present in the pharmaceutical dosage forms of the present invention in a concentration of about 0.01% to about 20%, about 0.1% to about 20%, about 0.1% to about 10%, about 0.1% to about 4%, about 0.5% to about 5%, about 0.5% to about 2%, about 0.65%, about 0.7%, about 0.75%, about 0.8%, or about 0.85% by weight of the dosage forms.

In some embodiments, the pharmaceutical dosage forms of the present invention further comprises a colorant. A "colorant" refers to a substance that can be added to the pharmaceutical dosage forms to enhance or modify their color or appearance. A colorant can also be added to the pharmaceutical dosage forms as a code or identifier (i.e., to indicate the manufacturer or dosage). Any type of colorant (i.e., "natural color" and/or "artificial color" such as F.D.&C. dyes) known to be "generally regarded as safe" by the U.S. Food and Drug Administration ("the FDA"), and thus generally used in the confectionary trade, or otherwise approved by the FDA for use in pharmaceutical preparations, can be used with the present invention.

Pharmaceutical dosage forms of the present invention have a hardness which makes them stable during preparation, packaging and storage. As used herein, "hardness" refers to the degree of force required to break, crumble or crack the pharmaceutical dosage forms. Hardness can be described in units of kilograms/mm$^2$ (kg/mm$^2$), pounds/in$^2$ (psi), pascals (Pa), Newtons/m$^2$ (N/m$^2$), kiloponds (kp), mohls or arbitrary units. The hardness of the pharmaceutical dosage forms can be measured, for example, using a tablet hardness tester.

In some embodiments, the pharmaceutical dosage forms of the present invention have a "low" hardness (i.e., a hardness of about 3 kp or less). The tablet hardness can be measured using, for example, a tablet hardness tester. Not being bound by any particular theory, such a low hardness can enhance water penetration into the pharmaceutical dosage forms of the present invention and facilitate their dispersion. In some embodiments, the pharmaceutical dosage forms of the present invention have a hardness of about 0.1 kp to about 5 kp, about 0.1 kp to about 3 kp, about 0.1 kp to about 2 kp, about 0.1 kp to about 1 kp, about 0.3 kp to about 5 kp, about 0.3 kp to about 3 kp, about 0.3 kp to about 2 kp, about 0.3 kp to about 1 kp, about 0.5 kp to about 5 kp, about 0.5 kp to about 3 kp, about 0.5 kp to about 2 kp, about 0.5 kp to about 0.1 kp, about 0.7 kp to about 5 kp, about 2 kp, or about 1 kp.

The pharmaceutical dosage forms of the present invention undergo disintegration without the use of effervescent agents. Suitable methods for determining the disintegration time and rate include the use of an USP disintegration tester, an automated disintegrating tester (e.g., available from Erweka America Corp., Annandale, N.J.) or a texture analyzer (e.g., available from Texture Technologies Corp., Scarsdale, N.Y.), and using methods described in, for example, El-Arini, S. K. and Clas S. D., "Evaluation of disintegration testing of different fast dissolving tablets using the texture analyzer," Pharm. Dev. Technol. 7:361-371 (2002), which is incorporated herein by reference in its entirety. Another suitable method for determining disintegration time is placing the formulation in a beaker of water and measuring the disintegration time and rate.

In some embodiments, the pharmaceutical dosage forms of the present invention disintegrate without effervescence in water in about 60 seconds or less, about 45 seconds or less, about 30 seconds or less, about 20 seconds or less, about 15 seconds or less, about 10 seconds or less, or about 8 seconds or less. In some embodiments, the pharmaceutical dosage forms of the present invention disintegrate without effervescence in water in about 5 seconds to about 60 seconds, about 5 seconds to about 45 seconds, about 5 seconds to about 30 seconds, about 5 seconds to about 15 seconds, about 5 seconds to about 10 seconds, or about 5 seconds to about 8 seconds.

The pharmaceutical dosage forms of the present invention also have good "mouth feel." As used herein, "mouth feel" refers to the presence of grit or debris in the buccal cavity after the dosage form has disintegrated. Mouth feel relates to the bulkiness of the remaining tablet mass after disintegration, and can be an important parameter for maintaining patient compliance. Suitable methods for measuring mouth feel for orally disintegrating solid dosage forms of the present invention include the use blinded screening comprising administering placebo formulations to volunteer subjects, as well as using a texture analyzer. Using a texture analyzer, mouth feel is measured as the difference (Δ) between the thickness (h) of a dosage form and the penetration distance (d) of water or liquid into the dosage form. Mouth feel improves as the value Δ is minimized.

As used herein, "dissolution" refers to the process by which the progestin equivalent to levonorgestrel goes into solution from the pharmaceutical dosage forms. In some embodiments, at least about 75%, at least about 80%, at least about 90%, or at least about 95% by weight of the progestin equivalent to levonorgestrel contained in the dosage forms of the present invention dissolves in a surfactant containing medium with a paddle speed of 75 rpm in about fifteen minutes or less. In some embodiments, at least about 75% to at least about 100% by weight of the progestin equivalent to levonorgestrel contained in the dosage forms of the present invention dissolves in a surfactant containing medium with a paddle speed of 75 rpm in about fifteen minutes or less. In some embodiments, greater than about 40% by weight of the progestin equivalent to levonorgestrel contained in the dosage forms of the present invention dissolves in a surfactant containing medium with a paddle speed of 75 rpm in about seven minutes or less. A suitable method for determining the dissolution rate is according to USP method II (FDA, 1997, Center for Drug Evaluation and Research, *Guidance for Industry: Dissolution Testing of Immediate Release Solid Oral Dosage Forms*, August 1997, which is incorporated herein by reference in its entirety).

In some embodiments, at least 75% by weight of the progestin equivalent to about 0.75 mg of levonorgestrel dissolves into solution in less than about 15 minutes when the dosage form is placed in a medium of 5 ppm Tween 80 in 900 mL of water according to USP method II at 75 rpm. In some embodiments, at least 75% by weight of the progestin equivalent to about 1.5 mg of levonorgestrel dissolves into solution in less than about 15 minutes when the dosage form is placed in a medium of 0.1% SDS in 0.1 N HCl according to USP method II at 75 rpm.

The in vivo concentration of progestin and its metabolites, as well as pharmacokinetic parameters can be determined by sampling the blood plasma of a subject after administration of the pharmaceutical dosage forms of the present invention. The non-effervescent, orally disintegrating solid pharmaceutical dosage forms of the present invention have excellent bioavailability. In some embodiments, the pharmaceutical dosage forms of the present invention have a bioavailability substantially equivalent to traditional oral dosage forms (e.g., oral tablets or oral solutions) containing progestin in a substantially equivalent dose (i.e., the pharmaceutical dosage forms of the present invention have a substantially equivalent $AUC_{inf}$). As used herein, "$AUC_{inf}$" refers to the Area Under the Concentration time curve, wherein the last concentration is extrapolated to baseline based on the rate constant for elimination.

Processes to Prepare the Dosage Forms

The present invention is also directed to a process for preparing a non-effervescent, orally disintegrating solid pharmaceutical dosage form, the process comprising mixing an ionic disintegrant and a progestin equivalent to about 0.5 mg to about 2 mg of levonorgestrel to form an initial mixture; adding to the initial mixture a hydrophilic water-insoluble non-ionic excipient to form a final mixture; and compressing the final mixture to produce the pharmaceutical dosage form; wherein the ionic disintegrant is present in a concentration of greater than 8% to about 60% by weight of the dosage form and the hydrophilic water-insoluble non-ionic excipient is present in a concentration of about 1% to about 20% by weight of the dosage form.

In one embodiment, the dosage forms can be prepared by passing a non-polymeric water-soluble carrier through a screen (using a #20 mesh screen) and mixing in a high-shear mixer. A progestin equivalent to levonorgestrel and at least one hydrophilic, water-insoluble ionic disintegrant (croscarmellose sodium, sodium starch glycolate, and/or polacrilin potassium) can be added, followed by mixing in a high-shear mixer. A flavorant and a sweetener, a binder and a glidant can be then added, mixed, screened (using a #20 mesh screen), and returned to the high-shear mixer for additional mixing. A lubricant can be combined, screened (using a #30 mesh screen), and added to the mixture, followed by additional mixing in a high-shear mixer. The resulting mixture can be compressed into orally disintegrating tablets. Formulation and manufacturing methods have been developed specific to a progestin equivalent to levonorgestrel orally disintegrating pharmaceutical dosage forms to facilitate high-volume production. The pharmaceutical dosage forms of the present invention are manufactured using dry mixing processes followed by direct compression. Prior to compression the dry compositions of the present invention are free-flowing, lubricated powders having a cohesiveness that enables the compositions to be used with automated equipment.

Methods of Treatment

The present invention is directed to a method of treating a female in need of emergency contraception, the method comprising: administering postcoitus to the female a first orally disintegrating solid pharmaceutical dosage form; and administering to the female within about 12 hours of administration of the first dosage form a second orally disintegrating solid pharmaceutical dosage form, wherein each of the first and second dosage forms comprises:
(a) a progestin equivalent to about 0.75 mg of levonorgestrel;
(b) an ionic disintegrant; and
(c) a hydrophilic water-insoluble non-ionic excipient; wherein the ionic disintegrant is present in a concentration of greater than 8% to about 60% by weight of the dosage form and the hydrophilic water-insoluble non-ionic excipient is present in a concentration of about 1% to about 20% by weight of the dosage form.

The present invention is directed to a method of treating a female in need of emergency contraception, the method comprising administering postcoitus to the female an orally disintegrating solid pharmaceutical dosage form comprising:
(a) a progestin equivalent to about 1.5 mg of levonorgestrel;
(b) an ionic disintegrant; and
(c) a hydrophilic water-insoluble non-ionic excipient; wherein the ionic disintegrant is present in a concentration of greater than 8% to about 60% by weight of the dosage form and the hydrophilic water-insoluble non-ionic excipient is present in a concentration of about 1% to about 20% by weight of the dosage form.

The terms "treat" and "treatment" refer to both therapeutic treatment and prophylactic, maintenance, or preventative measures, wherein the object is to prevent an undesired physiological condition, or obtain beneficial or desired clinical results. Treatment includes eliciting a clinically significant response, without excessive levels of side effects.

The term "emergency contraception" refers to a method of birth control that can be used after sexual intercourse. Emergency contraception is also known as emergency birth control, emergency postcoital contraception and postcoital contraception. The pharmaceutical dosage forms of the present invention can be administered immediately after, or within about 12 hours, within about 24 hours, within about 36 hours, within about 48 hours, within about 60 hours or within about 72 hours of sexual intercourse. In some embodiments, the pharmaceutical dosage forms of the present invention can be administered within about 84 hours, within about 96 hours, within about 108 hours, within about 120 hours of sexual intercourse.

In some embodiments, a first orally disintegrating solid pharmaceutical dosage form with a progestin equivalent to about 0.75 mg of levonorgestrel can be administered to a female in need of emergency contraception, and then a second dosage can be administered to the female, within about 96 hours postcoitus (or after intercourse or undesired insemination), within about 72 hours postcoitus, within about 48 hours postcoitus, or within about 24 hours postcoitus. For example, the first orally disintegrating solid pharmaceutical dosage form with a progestin equivalent to about 0.75 mg of levonorgestrel is administered to a female in need of emergency contraception, and a second dosage is administered to the same female within about 36 hours, within about 24 hours, or within about 12 hours after administration of the first dosage, and all the dosages are administered within about 96 hours postcoitus, within about 72 hours postcoitus, within about 48 hours postcoitus, or within about 24 hours postcoitus.

In some embodiments, a first orally disintegrating solid pharmaceutical dosage form with a progestin equivalent to about 0.75 mg of levonorgestrel can be administered to a female immediately postcoitus and a second orally disintegrating solid pharmaceutical dosage form with a progestin equivalent to about 0.75 mg of levonorgestrel can be administered within about 12 hours after the administration of the first orally disintegrating solid pharmaceutical dosage form. In some embodiments, a first orally disintegrating solid pharmaceutical dosage form with a progestin equivalent to about 0.75 mg of levonorgestrel can be administered to a female within about 72 hours postcoitus and a second orally disintegrating solid pharmaceutical dosage form with a progestin equivalent to about 0.75 mg of levonorgestrel can be administered within about 12 hours after the administration of the first orally disintegrating solid pharmaceutical dosage form. In some embodiments, an orally disintegrating solid pharmaceutical dosage form with a progestin equivalent to about 1.5 mg of levonorgestrel can be administered to a female immediately postcoitus. In some embodiments, an orally disintegrating solid pharmaceutical dosage form with a progestin equivalent to about 1.5 mg of levonorgestrel can be administered to a female within about 72 hours postcoitus.

The pharmaceutical dosage forms of the present invention can be administered alone or in conjunction with other medications and pharmaceutical compositions. In some embodiments, the present invention is directed to a method of treating a female in need of emergency contraception the progestin equivalent to levonorgestrel pharmaceutical dosage forms of the present invention.

The pharmaceutical dosage forms of the present invention can be administered alone or in conjunction with other medications and pharmaceutical compositions. In some embodiments, the present invention is directed to a method of treating a female in need of emergency contraception the progestin equivalent to levonorgestrel pharmaceutical dosage forms of the present invention.

As used herein, "administering to" refers to placing a pharmaceutical dosage form of the present invention in physical contact with the buccal cavity (i.e., the tongue, the buccal mucosa, the sublingual mucosa, etc.) of a subject in need thereof.

The following examples of processing conditions and parameters are given for the purpose of illustrating the present invention and shall not be construed as being limitations on the scope or spirit of the invention.

EXAMPLES

Example 1

Non-effervescent, orally disintegrating solid pharmaceutical dosage forms of the present invention containing levonorgestrel were prepared by the process outlined in FIG. 1 using the ingredients listed in Table 2.

The dosage forms were prepared by passing a non-polymeric water soluble carrier (mannitol and xylitol) through a screen (using a #20 mesh hand screen) in a high-shear mixer and mixing at low speed with the chopper on. Levonorgestrel and at least one hydrophilic, water-insoluble ionic disintegrant (croscarmellose sodium, sodium starch glycolate and/or polacrilin potassium) were added, followed by mixing at low speed with the chopper off. The drug container was rinsed with the hydrophilic, water-insoluble ionic disintegrant. A flavorant (strawberry flavor) and a sweetener (aspartame), a binder (microcrystalline cellulose) and a glidant (colloidal silicon dioxide) were then added, mixed, screened (using a #20 screen), and returned to the high-shear mixer for additional mixing. A lubricant (magnesium stearate and sodium stearyl fumarate) were combined, screened (using a #30 screen), and added to the mixture, followed by additional mixing in a high-shear mixer at low speed with the chopper off. The resulting mixture was compressed into tablets using a 9/32" flat faced bevel edged tooling to prepare the dosage forms.

TABLE 2

Ingredients and their amounts used to prepare non-effervescent, orally disintegrating solid pharmaceutical dosage forms of the present invention.

| # | Ingredients | Formulation 4 | Formulation 5 | Formulation 6 | Formulation 7 |
| | | Mg/dose | | | |
|---|---|---|---|---|---|
| 1 | Levonorgestrel, USP (Micronized) | 0.75 | 0.75 | 0.75 | 0.75 |
| 2 | Mannitol, USP (ParTeck ® M200) | 42 | 42 | 27 | 21.5 |
| 3 | Xylitol, NF (Xylisorb 300) | 6.1 | 6.1 | 6.1 | 6.1 |
| 4 | Polacrilin Potassium, NF (Amberlite IRP 88) | 15 | 10.5 | 10 | 10 |
| 5 | Croscarmellose Sodium, NF | — | 10 | — | — |
| 6 | Sodium Starch Glycolate, NF (Primojel) | — | — | 20 | — |
| 7 | Microcrystalline Cellulose, NF (Avicel PH-101) | 10.5 | 5 | 10.5 | 36 |
| 8 | Strawberry Flavor (SN302419) | 0.7 | 0.7 | 0.7 | 0.7 |
| 9 | Aspartame Powder, USP (Nutrasweet Powder) | 2.9 | 2.9 | 2.9 | 2.9 |

TABLE 2-continued

Ingredients and their amounts used to prepare non-effervescent, orally disintegrating solid pharmaceutical dosage forms of the present invention.

| # | Ingredients | Formulation 4 | Formulation 5 | Formulation 6 | Formulation 7 |
|---|---|---|---|---|---|
| | | | Mg/dose | | |
| 10 | Sodium Stearyl Fumarate, NF | 0.7 | 0.7 | 0.7 | 0.7 |
| 11 | Colloidal Silicon Dioxide, NF (Cab-O-Sil) | 1.1 | 1.1 | 1.1 | 1.1 |
| 12 | Magnesium stearate, NF | 0.25 | 0.25 | 0.25 | 0.25 |
| | Total Tablet Weight | 80 | 80 | 80 | 80 |

Figure 2:
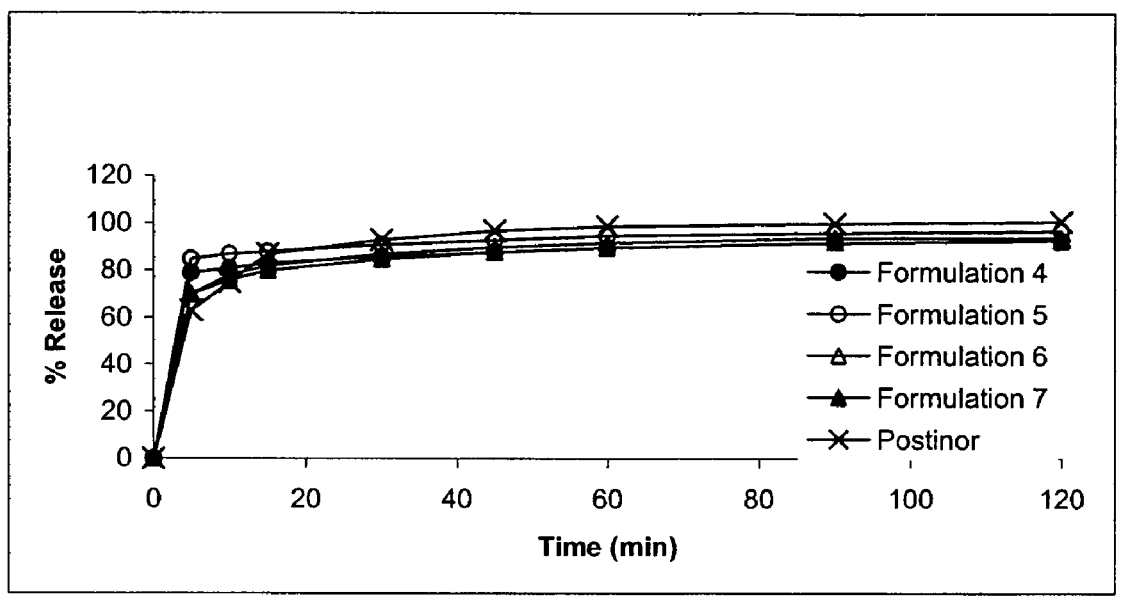
FIG. 2 is a graphical representation comparing the dissolution profiles of Formulation 4 (solid circle), Formulation 5 (hollow circle), Formulation 6 (hollow triangle), Formulation 7 (solid triangle) and POSTINOR®-2 (X). The dissolution profiles were taken in a medium of 5 ppm Tween 80 in 900 mL of water with a paddle speed of 75 rpm.

The dissolution profiles of Formulations 4-7 (without crospovidone) were taken in a medium of 5 ppm Tween 80 in 900 mL of water with a paddle speed of 75 rpm. The dissolution profiles of Formulations 4-7 as compared to Postinor (POSTINOR®-2, Schering) are listed in Table 3 and in FIG. 2.

TABLE 3

Dissolution profile for Formulations 4-7 and Postinor.

| Time (min) | Formulation 4 | Formulation 5 | Formulation 6 | Formulation 7 | Postinor |
|---|---|---|---|---|---|
| 0 | 0 | 0 | 0 | 0 | 0 |
| 5 | 79 | 85 | 70 | 70 | 63 |
| 10 | 81 | 87 | 78 | 76 | 75 |
| 15 | 83 | 88 | 82 | 80 | 87 |
| 30 | 86 | 91 | 87 | 85 | 93 |
| 45 | 88 | 93 | 90 | 88 | 97 |
| 60 | 90 | 95 | 92 | 90 | 99 |
| 90 | 92 | 96 | 94 | 92 | 100 |
| 120 | 93 | 97 | 94 | 93 | 101 |

Hardness was measured for Formulations 4-7. In addition, disintegration times were measured by USP disintegration tester. The hardness and disintegration times of Formulations 4-7 are listed in Tables 4.

TABLE 4

Disintegration Time of Formulations 4-7 by USP Disintegration Tester.

| USP-Tester Hardness (kp) | Formulation 4 | Formulation 5 | Formulation 6 | Formulation 7 |
|---|---|---|---|---|
| | | DT (sec) | | |
| 0.5 | 7 | 7 | 5 | 4 |
| 1 | 8 | 7 | 9 | 4 |
| 1.5 | 8 | — | 11 | 4 |
| 2 | 11 | — | 19 | 4 |

Comparative Example 1

Non-effervescent, orally disintegrating solid pharmaceutical dosage forms of the present invention containing levonorgestrel and a water insoluble non-ionic disintegrant (crospovidone) were prepared by the process outlined in FIG. 1 using the ingredients listed in Table 5.

The dosage forms were prepared by passing a non-polymeric water soluble carrier (mannitol and xylitol) through a screen (using a #20 mesh hand screen) in a high-shear mixer and mixing at low speed with the chopper on. Levonorgestrel and at least one hydrophilic, water-insoluble non-ionic disintegrant (crospovidone) were added, followed by mixing at low speed with the chopper off. The drug container was rinsed with the hydrophilic, water-insoluble non-ionic disintegrant. A flavorant (strawberry flavor) and a sweetener (aspartame), a binder (microcrystalline cellulose) and a glidant (colloidal silicon dioxide) were then added, mixed, screened (using a #20 screen), and returned to the high-shear mixer for additional mixing. A lubricant (magnesium stearate and sodium stearyl fumarate) were combined, screened (using a #30 screen), and added to the mixture, followed by additional mixing in a high-shear mixer at low speed with the chopper off. The resulting mixture was compressed into tablets using a 9/32" flat faced bevel edged tooling to prepare the dosage forms.

TABLE 5

Ingredients and their amounts used for the formulation prepare non-effervescent, orally disintegrating solid pharmaceutical dosage forms with the non-ionic disintegrant crospovidone.

| # | Ingredients | Formulation 1 | Formulation 2 | Formulation 3 |
|---|---|---|---|---|
| | | | Mg/dose | |
| 1 | Levonorgestrel, USP (Micronized) | 0.75 | 0.75 | 0.75 |
| 2 | Mannitol, USP (ParTeck ® M200) | 41.95 | 41.95 | 42 |
| 3 | Xylitol, NF (Xylisorb 300) | 6.1 | 6.1 | 6.1 |
| 4 | Crospovidone, NF (Polyplasdone XL) | 21.5 | 22.2 | 21.9 |
| 5 | Microcrystalline Cellulose, NF (Avicel PH-101) | 3.6 | 3.6 | 3.6 |
| 6 | Strawberry Flavor (SN302419) | 0.7 | 0.7 | 0.7 |
| 7 | Aspartame Powder, USP (Nutrasweet Powder) | 2.9 | 2.9 | 2.9 |
| 8 | Sodium Stearyl Fumarate, NF | 0.7 | 0.7 | 0.7 |
| 9 | Colloidal Silicon Dioxide, NF (Cab-O-Sil) | 1.1 | 1.1 | 1.1 |
| 10 | Magnesium stearate, NF | 0.7 | — | 0.25 |
| | Total Tablet Weight | 80 | 80 | 80 |

Figure 3:
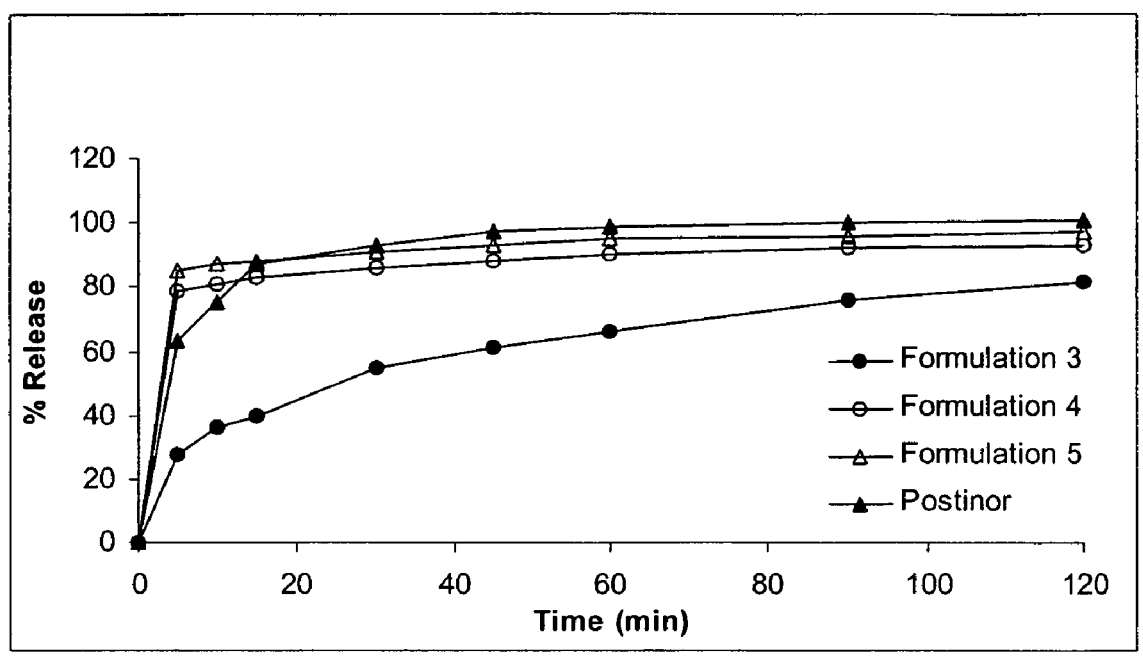
FIG. 3 is a graphical representation comparing the dissolution profiles of Formulation 3 (solid circle) with Formulation 4 (hollow circle), Formulation 5 (hollow triangle) and POSTINOR®-2 (solid triangle). The dissolution profiles were taken in a medium of 5 ppm Tween 80 in 900 mL of water with a paddle speed of 75 rpm.

The dissolution profiles of Formulation 3 (levonorgestrel and crospovidone) and Formulations 4 (levonorgestrel and polacrilin potassium) and 5 (levonorgestrel and croscarmellose sodium/polacrilin potassium) were taken in a medium of 5 ppm Tween 80 in 900 mL of water with a paddle speed of 75 rpm. The dissolution profiles of Formulations 3-5 as compared to Postinor (POSTINOR®-2, Schering) are listed in Table 6 and in FIG. 3.

TABLE 6

Formulation 3 vs. Formulation 4 or Formulation 5: the effect of the non-ionic disintegrant crospovidone, NF on dissolution rate as compared to the ionic disintegrants, Polacrilin potassium and croscarmellose sodium.

| Time (min) | Formulation 3 | Formulation 4 | Formulation 5 | Postinor |
|---|---|---|---|---|
|  |  | % Released |  |  |
| 0 | 0 | 0 | 0 | 0 |
| 5 | 28 | 79 | 85 | 63 |
| 10 | 36 | 81 | 87 | 75 |
| 15 | 40 | 83 | 88 | 87 |
| 30 | 55 | 86 | 91 | 93 |
| 45 | 61 | 88 | 93 | 97 |
| 60 | 66 | 90 | 95 | 99 |
| 90 | 76 | 92 | 96 | 100 |
| 120 | 82 | 93 | 97 | 101 |

Example 2

Non-effervescent, orally disintegrating solid pharmaceutical dosage forms of the present invention containing levonorgestrel were prepared by the process outlined in FIG. 1 using the ingredients listed in Table 7.

The dosage forms were prepared by passing a non-polymeric water soluble carrier (mannitol and xylitol) through a screen (using a #20 mesh hand screen) in a high-shear mixer and mixing at low speed with the chopper on. Levonorgestrel and at least one hydrophilic, water-insoluble ionic disintegrant (croscarmellose sodium and polacrilin potassium) were added, followed by mixing at low speed with the chopper off. The drug container was rinsed with the hydrophilic, water-insoluble ionic disintegrant. A flavorant (strawberry flavor) and a sweetener (aspartame), a binder (microcrystalline cellulose) and a glidant (colloidal silicon dioxide) were then added, mixed, screened (using a #20 screen), and returned to the high-shear mixer for additional mixing. A lubricant (magnesium stearate and sodium stearyl fumarate) were combined, screened (using a #30 screen), and added to the mixture, followed by additional mixing in a high-shear mixer at low speed with the chopper off. The resulting mixture was compressed into tablets using a 9/32" flat faced bevel edged tooling to prepare the dosage forms.

TABLE 7

Ingredients and their amounts used to prepare non-effervescent, orally disintegrating solid pharmaceutical dosage forms of the present invention.

| # | Composition | Formulation 5 | Formulation 8 |
|---|---|---|---|
| 1 | Levonorgestrel, USP (Micronized) | 0.75 | 0.75 |
| 2 | Mannitol, USP (ParTeck ® M200) | 42 | 30.5 |
| 3 | Xylitol, NF (Xylisorb 300) | 6.1 | 6.1 |
| 4 | Polacrilin Potassium, NF (Amberlite IRP 88) | 10.5 | 7 |
| 5 | Croscarmellose Sodium, NF | 10 | 20 |
| 6 | Microcrystalline Cellulose, NF (Avicel PH-101) | 5 | 10 |
| 7 | Strawberry Flavor (SN302419) | 0.7 | 0.7 |
| 8 | Aspartame Powder, USP (Nutrasweet Powder) | 2.9 | 2.9 |
| 9 | Sodium Stearyl Fumarate, NF | 0.7 | 0.7 |
| 10 | Colloidal Silicon Dioxide, NF (Cab-O-Sil) | 1.1 | 1.1 |
| 11 | Magnesium stearate, NF | 0.25 | 0.25 |
|  | Total Tablet Weight | 80 | 80 |

Figure 4:
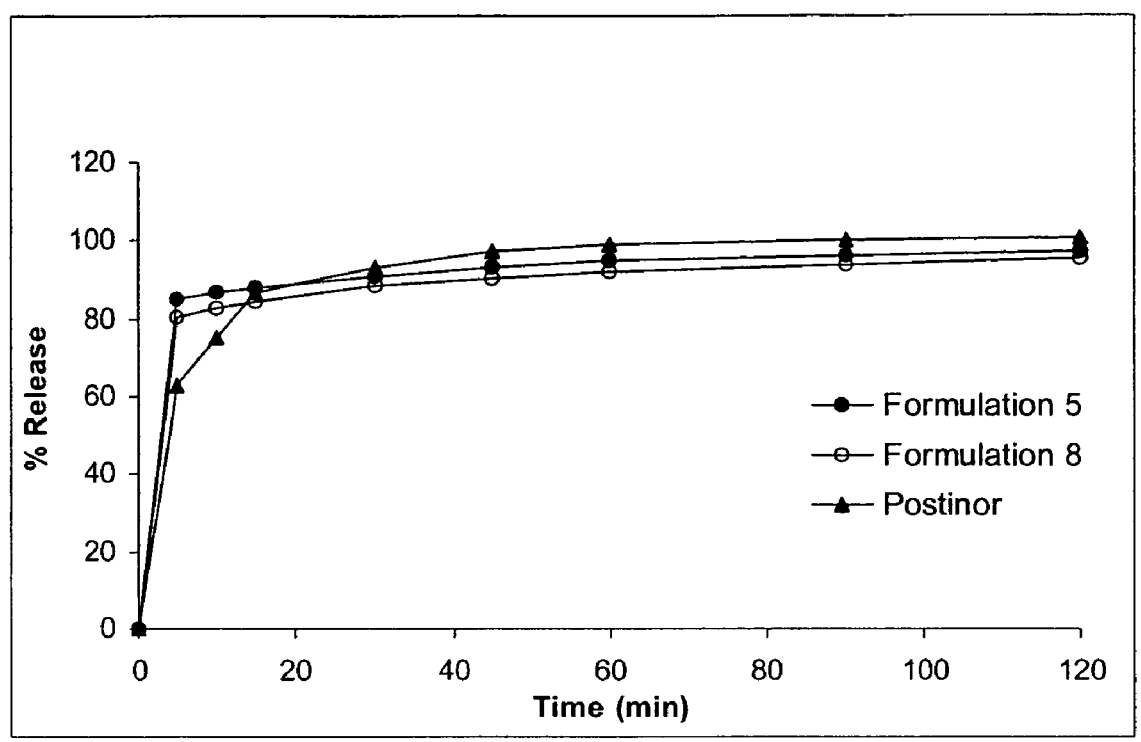
FIG. 4 is a graphical representation comparing the dissolution profiles of Formulation 5 (solid circle) with Formulation 8 (hollow circle) and POSTINOR®-2 (solid triangle). The dissolution profiles were taken in a medium of 5 ppm Tween 80 in 900 mL of water with a paddle speed of 75 rpm.

The dissolution profiles of Formulation 5 and Formulation 8 were taken in a medium of 5 ppm Tween 80 in 900 mL of water with a paddle speed of 75 rpm. The dissolution profiles of Formulations 5 and 8 as compared to Postinor (POSTINOR®-2, Schering) are listed in Table 8 and in FIG. 4.

TABLE 8

Dissolution profile comparison for Formulation 5, Formulation 8 and Postinor.

| Time (min) | Formulation 5 | Formulation 8 | Postinor |
|---|---|---|---|
| 0 | 0 | 0 | 0 |
| 5 | 85 | 80 | 63 |
| 10 | 87 | 83 | 75 |
| 15 | 88 | 85 | 87 |
| 30 | 91 | 88 | 93 |
| 45 | 93 | 90 | 97 |
| 60 | 95 | 92 | 99 |
| 90 | 96 | 94 | 100 |
| 120 | 97 | 95 | 101 |

Hardness was measured for Formulations 5 and 8. In addition, disintegration times were measured by USP disintegration tester. The hardness and disintegration times of Formulations 5 and 8 are listed in Table 9.

TABLE 9

Comparison of disintegration times for Formulations 5 and 8 by USP disintegration tester.

| | USP-Tester | |
|---|---|---|
| | Formulation 5 | Formulation 8 |
| Hardness (kp) | DT (sec) | |
| 0.5 | 7 | 10 |
| 1.0 | 7 | 11 |
| 1.5 |  | 12 |
| 2.0 |  | 16 |

Example 3

Non-effervescent, orally disintegrating solid pharmaceutical dosage forms of the present invention containing levonorgestrel and a water insoluble non-ionic disintegrant (crospovidone) were prepared by the process outlined in FIG. 1 using the ingredients listed in Table 10.

The dosage forms were prepared by passing a non-polymeric water soluble carrier (mannitol and xylitol) through a screen (using a #20 mesh hand screen) in a high-shear mixer and mixing at low speed with the chopper on. Levonorgestrel and at least one hydrophilic, water-insoluble non-ionic disintegrant (crospovidone) were added, followed by mixing at low speed with the chopper off. The drug container was rinsed with the hydrophilic, water-insoluble non-ionic disintegrant. A flavorant (strawberry flavor) and a sweetener (aspartame), a binder (microcrystalline cellulose) and a glidant (colloidal silicon dioxide) were then added, mixed, screened (using a #20 screen), and returned to the high-shear mixer for additional mixing. A lubricant (magnesium stearate and sodium stearyl fumarate) were combined, screened (using a #30 screen), and added to the mixture, followed by additional mixing in a high-shear mixer at low speed with the chopper off. The resulting mixture was compressed into tablets using a 9/32" flat faced bevel edged tooling to prepare the dosage forms.

TABLE 10

Ingredients and their amounts used to prepare non-effervescent, orally disintegrating solid pharmaceutical dosage forms with levonorgestrel and the water insoluble non-ionic disintegrant crospovidone.

| # | Ingredients | Formulation 1 | Formulation 9 Mg/dose | Formulation 10 |
|---|---|---|---|---|
| 1 | Levonorgestrel, USP (Micronized) | 0.75 | 0.75 | 0.75 |
| 2 | Mannitol, USP (ParTeck ® M200) | 41.95 | 31.95 | 31.95 |
| 3 | Xylitol, NF (Xylisorb 300) | 6.1 | 6.1 | 6.1 |
| 4 | Polacrilin Potassium, NF (Amberlite IRP 88) | — | 10 | — |
| 5 | Saccharin Sodium, USP | — | — | 10 |
| 6 | Crospovidone, NF (Polyplasdone XL) | 21.5 | 21.5 | 21.5 |
| 7 | Microcrystalline Cellulose, NF (Avicel PH-101) | 3.6 | 3.6 | 3.6 |
| 8 | Strawberry Flavor (SN302419) | 0.7 | 0.7 | 0.7 |
| 9 | Aspartame Powder, USP (Nutrasweet Powder) | 2.9 | 2.9 | 2.9 |
| 10 | Sodium Stearyl Fumarate, NF | 0.7 | 0.7 | 0.7 |
| 11 | Colloidal Silicon Dioxide, NF (Cab-O-Sil) | 1.1 | 1.1 | 1.1 |
| 12 | Magnesium stearate, NF | 0.7 | 0.7 | 0.7 |
|   | Total Tablet Weight | 80 | 80 | 80 |

Figure 5:
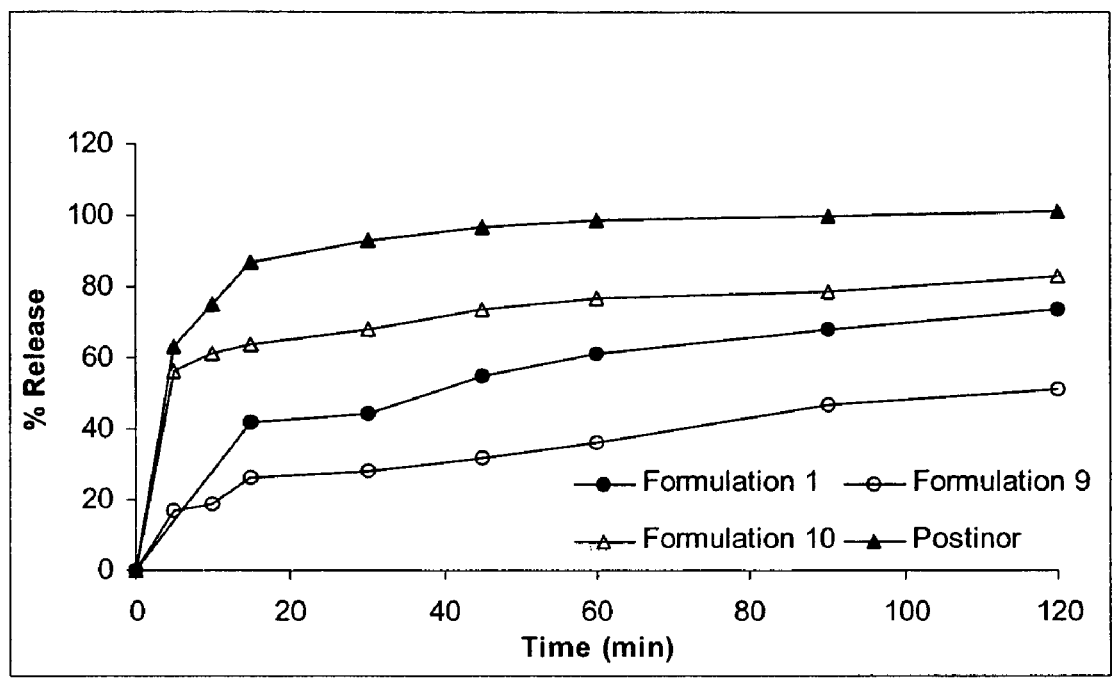
FIG. 5 is a graphical representation comparing the dissolution profiles of Formulation 1 (solid circle), Formulation 9 (hollow circle), Formulation 10 (hollow triangle) and POSTINOR®-2 (solid triangle). The dissolution profiles were taken in a medium of 5 ppm Tween 80 in 900 mL of water with a paddle speed of 75 rpm.

The dissolution profiles of Formulation 1 (crospovidone), Formulation 9 (crospovidone and polacrilin potassium) and Formulation 10 (crospovidone and saccharin sodium) were taken in a medium of 5 ppm Tween 80 in 900 mL of water with a paddle speed of 75 rpm. The dissolution profiles of Formulations 1, 9 and 10 as compared to Postinor (POSTINOR-2, Schering) are listed in Table 11 and in FIG. 5.

TABLE 11

Dissolution profiles comparing Formulation 1, Formulation 9, Formulation 10 and Postinor.

| Time (min) | Formulation 1 | Formulation 9 | Formulation 10 | Postinor |
|---|---|---|---|---|
| 0 | 0 | 0 | 0 | 0 |
| 5 | NA | 17 | 56 | 63 |
| 10 | NA | 19 | 61 | 75 |
| 15 | 42 | 26 | 64 | 87 |
| 30 | 45 | 28 | 68 | 93 |
| 45 | 55 | 32 | 74 | 97 |
| 60 | 61 | 36 | 77 | 99 |
| 90 | 68 | 47 | 79 | 100 |
| 120 | 74 | 51 | 83 | 101 |

Hardness was measured for Formulations 9 and 10. In addition, disintegration times were measured by placing the formulation in a beaker of water and measuring disintegration time of the formulation. The hardness and disintegration times of Formulations 9 and 10 are shown in Table 12.

TABLE 12

Comparison of disintegration times for Formulations 9 and 10 in a beaker of water.

| | Beaker | |
|---|---|---|
| | Formulation 9 | Formulation 10 |
| Hardness (kp) | DT (sec) | |
| 0.5 | 16 | 14 |
| 1.0 | 18 | 17 |
| 1.5 | 21 | 21 |
| 2.0 | 22 | 22 |

Example 4

Non-effervescent, orally disintegrating solid pharmaceutical dosage forms of the present invention containing levonorgestrel were prepared by the process outlined in FIG. 1 using the ingredients listed in Table 13.

The dosage forms were prepared by passing a non-polymeric water soluble carrier (mannitol and xylitol) through a screen (using a #20 mesh hand screen) in a high-shear mixer and mixing at low speed with the chopper on. Levonorgestrel and at least one hydrophilic, water-insoluble ionic disintegrant (croscarmellose sodium or sodium starch glycolate) were added, followed by mixing at low speed with the chopper off. The drug container was rinsed with the hydrophilic, water-insoluble ionic disintegrant. A flavorant (strawberry flavor) and a sweetener (aspartame), a binder (microcrystalline cellulose) and a glidant (colloidal silicon dioxide) were then added, mixed, screened (using a #20 screen), and returned to the high-shear mixer for additional mixing. A lubricant (magnesium stearate and sodium stearyl fumarate) were combined, screened (using a #30 screen), and added to the mixture, followed by additional mixing in a high-shear mixer at low speed with the chopper off. The resulting mixture was compressed into tablets using a 9/32" flat faced bevel edged tooling to prepare the dosage forms.

TABLE 13

Ingredients and their amounts used to prepare non-effervescent, orally disintegrating solid pharmaceutical dosage forms of the present invention.

| # | Composition | Formulation 11 | Formulation 12 |
|---|---|---|---|
| 1 | Levonorgestrel, USP (Micronized) | 0.75 | 0.75 |
| 2 | Mannitol, USP (ParTeck ® M200) | 37.5 | 37 |
| 3 | Xylitol, NF (Xylisorb 300) | 6.1 | 6.1 |
| 4 | Croscarmellose Sodium, NF | 20 | — |
| 5 | Sodium Starch Glycolate, NF (Primojel) | — | 20 |
| 6 | Microcrystalline Cellulose, NF (Avicel PH-101) | 10 | 10.5 |
| 7 | Strawberry Flavor (SN302419) | 0.7 | 0.7 |
| 8 | Aspartame Powder, USP (Nutrasweet Powder) | 2.9 | 2.9 |
| 9 | Sodium Stearyl Fumarate, NF | 0.7 | 0.7 |
| 10 | Colloidal Silicon Dioxide, NF (Cab-O-Sil) | 1.1 | 1.1 |
| 11 | Magnesium stearate, NF | 0.25 | 0.25 |
|   | Total Tablet Weight | 80 | 80 |

Figure 6:
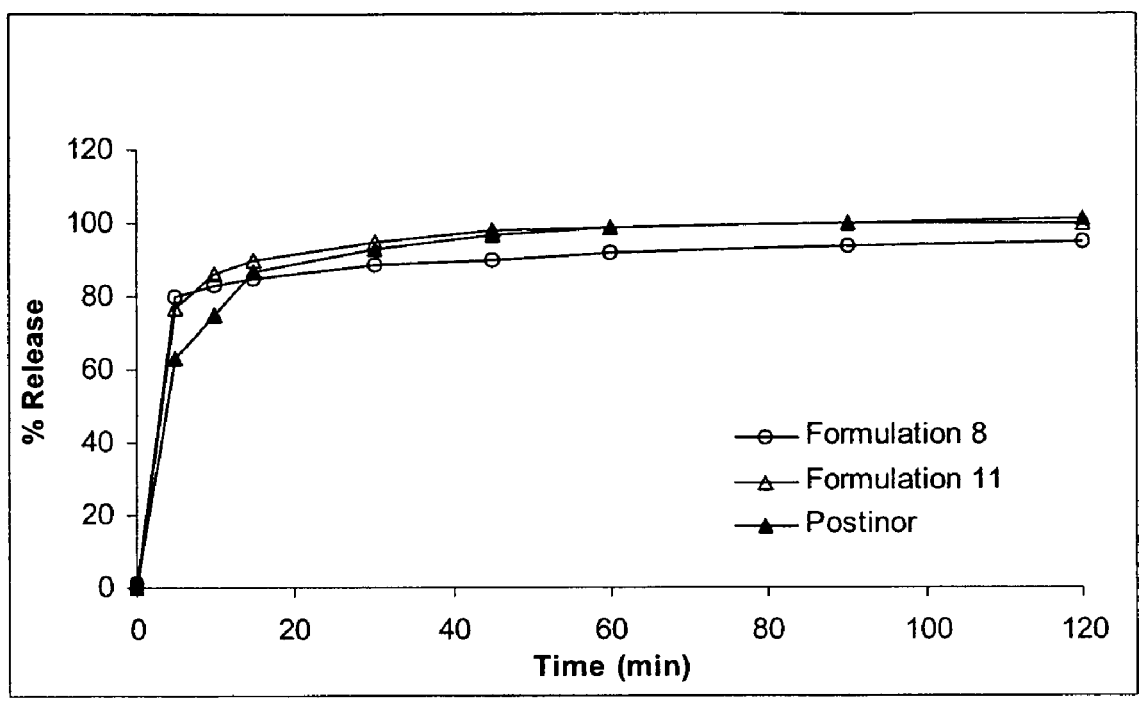
FIG. 6 is a graphical representation comparing the dissolution profiles of Formulation 8 (hollow circle), Formulation 11 (hollow triangle) and POSTINOR®-2 (solid triangle). The dissolution profiles were taken in a medium of 5 ppm Tween 80 in 900 mL of water with a paddle speed of 75 rpm.

The dissolution profiles of Formulation 8 (levonorgestrel/croscarmellose sodium/polacrilin potassium) and Formulation 11 (levonorgestrel/croscarmellose sodium) were taken in a medium of 5 ppm Tween 80 in 900 mL of water with a paddle speed of 75 rpm. The dissolution profiles of Formulations 8 and 11 as compared to Postinor (POSTINOR®-2, Schering) are listed in Table 14 and in FIG. 6.

TABLE 14

Dissolution profiles comparison between Formulation 8, Formulation 11 and Postinor.

| Time (min) | Formulation 8 | Formulation 11 | Postinor |
|---|---|---|---|
| 0 | 0 | 0 | 0 |
| 5 | 80 | 77 | 63 |
| 10 | 83 | 86 | 75 |
| 15 | 85 | 90 | 87 |
| 30 | 88 | 95 | 93 |
| 45 | 90 | 98 | 97 |
| 60 | 92 | 99 | 99 |
| 90 | 94 | 100 | 100 |
| 120 | 95 | 100 | 101 |

Figure 7:
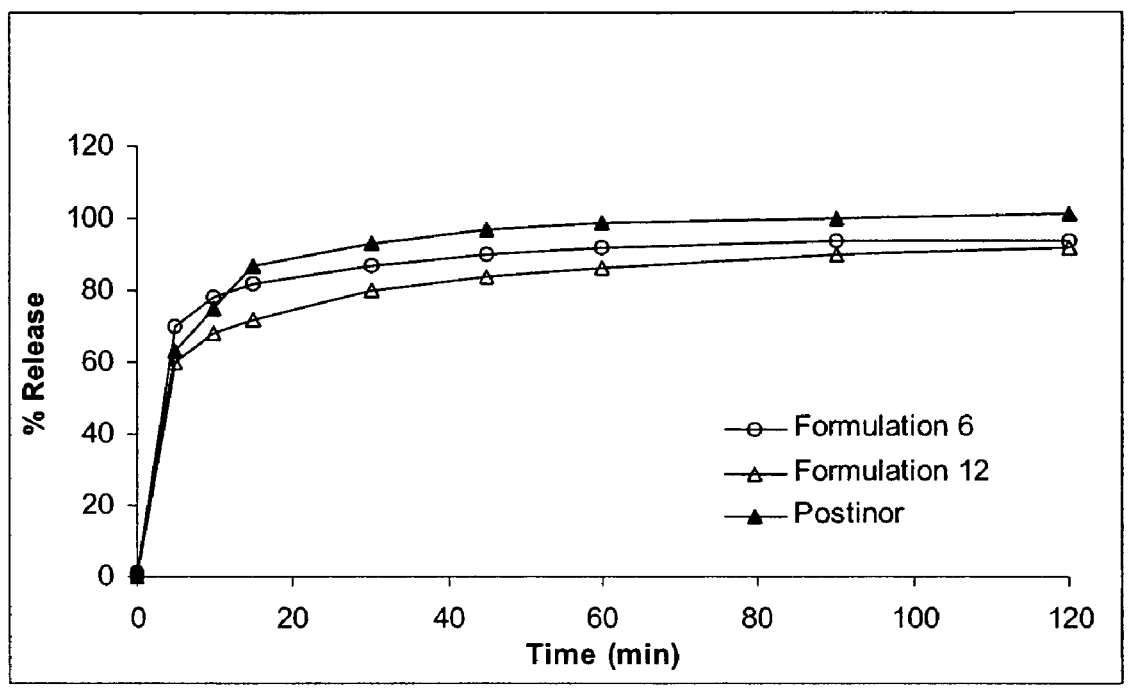
FIG. 7 is a graphical representation comparing the dissolution profiles of Formulation 6 (hollow circle), Formulation 12 (hollow triangle) and POSTINOR®-2 (solid triangle). The dissolution profiles were taken in a medium of 5 ppm Tween 80 in 900 mL of water with a paddle speed of 75 rpm.

The dissolution profiles of Formulation 6 (levonorgestrel/sodium starch glycolate/polacrilin potassium) and Formulation 12 (levonorgestrel/sodium starch glycolate) were taken in a medium of 5 ppm Tween 80 in 900 mL of water with a paddle speed of 75 rpm. The dissolution profiles of Formulations 6 and 12 as compared to Postinor (POSTINOR®-2, Schering) are listed in Table 15 and in FIG. 7.

TABLE 15

Dissolution profiles comparison between Formulation 6, Formulation 12 and Postinor.

| Time (min) | Formulation 6 | Formulation 12 | Postinor |
|---|---|---|---|
| 0 | 0 | 0 | 0 |
| 5 | 70 | 60 | 63 |
| 10 | 78 | 68 | 75 |
| 15 | 82 | 72 | 87 |
| 30 | 87 | 80 | 93 |
| 45 | 90 | 84 | 97 |
| 60 | 92 | 86 | 99 |
| 90 | 94 | 90 | 100 |
| 120 | 94 | 92 | 101 |

Example 5

Non-effervescent, orally disintegrating solid pharmaceutical dosage forms of the present invention containing levonorgestrel were prepared by the process outlined in FIG. 1 using the ingredients listed in Table 16.

The dosage forms were prepared by passing a non-polymeric water soluble carrier (mannitol and xylitol) through a screen (using a #20 mesh hand screen) in a high-shear mixer and mixing at low speed with the chopper on. Levonorgestrel and at least one hydrophilic, water-insoluble ionic disintegrant (croscarmellose sodium and/or polacrilin potassium) were added, followed by mixing at low speed with the chopper off. The drug container was rinsed with the hydrophilic, water-insoluble ionic disintegrant. A flavorant (strawberry flavor) and a sweetener (aspartame), a binder (microcrystalline cellulose) and a glidant (colloidal silicon dioxide) were then added, mixed, screened (using a #20 screen), and returned to the high-shear mixer for additional mixing. A lubricant (magnesium stearate and sodium stearyl fumarate) were combined, screened (using a #30 screen), and added to the mixture, followed by additional mixing in a high-shear mixer at low speed with the chopper off. The resulting mixture was compressed into tablets using a 9/32" flat faced bevel edged tooling to prepare the dosage forms.

TABLE 16

Ingredients and their amounts used to prepare non-effervescent, orally disintegrating solid pharmaceutical dosage forms of the present invention.

| # | Composition | Formulation 5 | Formulation 8 | Formulation 11 |
|---|---|---|---|---|
| 1 | Levonorgestrel, USP (Micronized) | 0.75 | 0.75 | 0.75 |
| 2 | Mannitol, USP (ParTeck ® M200) | 42 | 30.5 | 37.5 |
| 3 | Xylitol, NF (Xylisorb 300) | 6.1 | 6.1 | 6.1 |
| 4 | Polacrilin Potassium, NF (Amberlite IRP 88) | 10.5 | 7 | — |
| 5 | Croscarmellose Sodium, NF | 10 | 20 | 20 |
| 6 | Microcrystalline Cellulose, NF (Avicel PH-101) | 5 | 10 | 10 |
| 7 | Strawberry Flavor (SN302419) | 0.7 | 0.7 | 0.7 |
| 8 | Aspartame Powder, USP (Nutrasweet Powder) | 2.9 | 2.9 | 2.9 |
| 9 | Sodium Stearyl Fumarate, NF | 0.7 | 0.7 | 0.7 |
| 10 | Colloidal Silicon Dioxide, NF (Cab-O-Sil) | 1.1 | 1.1 | 1.1 |
| 11 | Magnesium stearate, NF | 0.25 | 0.25 | 0.25 |
|  | Total Tablet Weight | 80 | 80 | 80 |

Figure 8:
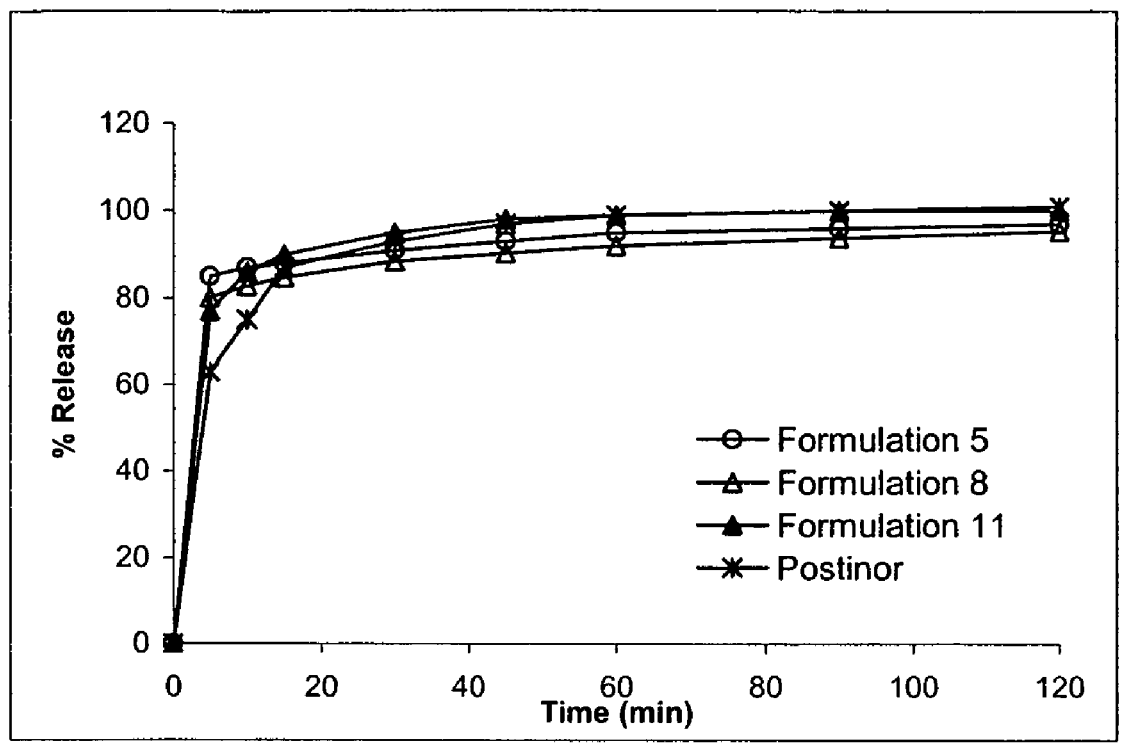
FIG. 8 is a graphical representation comparing the dissolution profiles of Formulation 5 (hollow circle), Formulation 8 (hollow triangle), Formulation 11 (solid triangle) and POSTINOR®-2 (solid star). The dissolution profiles were taken in a medium of 5 ppm Tween 80 in 900 mL of water with a paddle speed of 75 rpm.

The dissolution profiles of Formulation 5 (levonorgestrel/croscarmellose sodium/polacrilin potassium), Formulation 8 (levonorgestrel/croscarmellose sodium/polacrilin potassium), and Formulation 11 (levonorgestrel/croscarmellose sodium) were taken in a medium of 5 ppm Tween 80 in 900 mL of water with a paddle speed of 75 rpm. The dissolution profiles of Formulations 5, 8, and 11 as compared to Postinor (POSTINOR®-2, Schering) are listed in Table 17 and in FIG. 8.

TABLE 17

Dissolution profiles of Formulations 5, 8, 11 and Postinor.

| Time (min) | Formulation 5 | Formulation 8 | Formulation 11 | Postinor |
|---|---|---|---|---|
| 0 | 0 | 0 | 0 | 0 |
| 5 | 85 | 80 | 77 | 63 |
| 10 | 87 | 83 | 86 | 75 |
| 15 | 88 | 85 | 90 | 87 |
| 30 | 91 | 88 | 95 | 93 |
| 45 | 93 | 90 | 98 | 97 |
| 60 | 95 | 92 | 99 | 99 |
| 90 | 96 | 94 | 100 | 100 |
| 120 | 97 | 95 | 100 | 101 |

Example 6

Non-effervescent, orally disintegrating solid pharmaceutical dosage forms of the present invention containing levonorgestrel were prepared by the process outlined in FIG. 1 using the ingredients listed in Table 18.

The dosage forms were prepared by passing a non-polymeric water soluble carrier (mannitol and xylitol) through a screen (using a #20 mesh hand screen) in a high-shear mixer and mixing at low speed with the chopper on. For Formulation 7, levonorgestrel and at least one hydrophilic, water-insoluble ionic disintegrant (polacrilin potassium) were added, followed by mixing at low speed with the chopper off. The drug container was rinsed with the hydrophilic, water-insoluble ionic disintegrant. For Formulation 14, no hydrophilic, water-insoluble ionic disintegrant was added nor was the drug container rinsed with a hydrophilic, water-insoluble ionic disintegrant. A flavorant (strawberry flavor) and a sweetener (aspartame), a binder (microcrystalline cellulose) and a glidant (colloidal silicon dioxide) were then added, mixed, screened (using a #20 screen), and returned to the high-shear mixer for additional mixing. A lubricant (magnesium stearate and sodium stearyl fumarate) were combined, screened (using a #30 screen), and added to the mixture, followed by additional mixing in a high-shear mixer at low speed with the chopper off. The resulting mixture was compressed into tablets using a 9/32" flat faced bevel edged tooling to prepare the dosage forms.

TABLE 18

Ingredients and their amounts used to prepare non-effervescent, orally disintegrating solid pharmaceutical dosage forms of the present invention.

| Ingredients | Formulation 7 Mg/dose | Formulation 14 Mg/dose |
|---|---|---|
| Levonorgestrel, USP (Micronized) | 0.75 | 0.75 |
| Mannitol, USP (ParTeck ® M200) | 21.5 | 28.2 |
| Xylitol, NF (Xylisorb 300) | 6.1 | 6.1 |
| Polacrilin Potassium, NF (Amberlite IRP 88) | 10 | — |
| Microcrystalline Cellulose, NF (Avicel PH-101) | 36 | 40 |
| Strawberry Flavor (SN302419) | 0.7 | 0.7 |
| Aspartame Powder, USP (Nutrasweet Powder) | 2.9 | 2.9 |
| Sodium Stearyl Fumarate, NF | 0.7 | — |
| Colloidal Silicon Dioxide, NF (Cab-O-Sil) | 1.1 | 1.1 |
| Magnesium stearate, NF | 0.25 | 0.25 |
| Total Tablet Weight | 80 | 80 |

Figure 9:
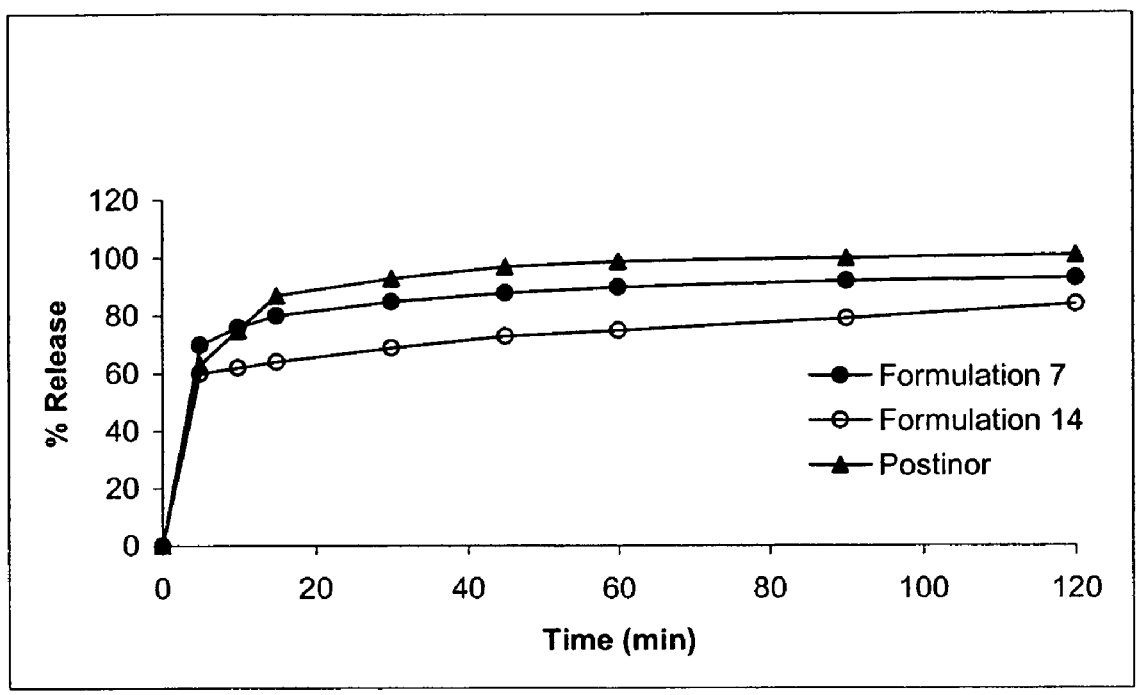
FIG. 9 is a graphical representation comparing the dissolution profiles of Formulation 7 (solid circle), Formulation 14 (hollow circle), and POSTINOR®-2 (solid triangle). The dissolution profiles were taken in a medium of 5 ppm Tween 80 in 900 mL of water with a paddle speed of 75 rpm.

The dissolution profiles of Formulation 7 and Formulation 14 were taken in a medium of 5 ppm Tween 80 in 900 mL of water with a paddle speed of 75 rpm. The dissolution profiles of Formulations 7 and 14 as compared to Postinor (POSTINOR®-2, Schering) are listed in Table 19 and in FIG. 9.

TABLE 19

Dissolution profiles of Formulations 7, Formulation 14 and Postinor.

| Time (min) | Formulation 7 | Formulation 14 | Postinor |
|---|---|---|---|
| 0 | 0 | 0 | 0 |
| 5 | 70 | 60 | 63 |
| 10 | 76 | 62 | 75 |
| 15 | 80 | 64 | 87 |
| 30 | 85 | 69 | 93 |
| 45 | 88 | 73 | 97 |
| 60 | 90 | 75 | 99 |
| 90 | 92 | 79 | 100 |
| 120 | 93 | 84 | 101 |

Example 7

Non-effervescent, orally disintegrating solid pharmaceutical dosage forms of the present invention containing levonorgestrel were prepared by the process outlined in FIG. 1 using the ingredients listed in Table 20.

The dosage forms were prepared by passing a non-polymeric water soluble carrier (mannitol and xylitol) through a screen (using a #20 mesh hand screen) in a high-shear mixer and mixing at low speed with the chopper on. Levonorgestrel and at least one hydrophilic, water-insoluble ionic disintegrant (croscarmellose sodium and polacrilin potassium) were added, followed by mixing at low speed with the chopper off. The drug container was rinsed with the hydrophilic, water-insoluble ionic disintegrant. A flavorant (strawberry flavor) and a sweetener (aspartame), a binder (microcrystalline cellulose) and a glidant (colloidal silicon dioxide) were then added, mixed, screened (using a #20 screen), and returned to the high-shear mixer for additional mixing. A lubricant (magnesium stearate and sodium stearyl fumarate) were combined, screened (using a #30 screen), and added to the mixture, followed by additional mixing in a high-shear mixer at low speed with the chopper off. The resulting mixture was compressed into tablets using a 9/32" flat faced bevel edged tooling to prepare the dosage forms.

TABLE 20

Ingredients and their amounts used to prepare non-effervescent, orally disintegrating solid pharmaceutical dosage forms of the present invention.

| # | Composition | Formulation 16 | Formulation 17 | Formulation 18 |
|---|---|---|---|---|
| 1 | Levonorgestrel, USP (Micronized) | 1.5 | 1.5 | 1.5 |
| 2 | Mannitol, USP (ParTeck ® M200) | 44.8 | 38.9 | 42.9 |
| 3 | Xylitol, NF (Xylisorb 300) | 6.1 | 6.1 | 6.1 |
| 4 | Polacrilin Potassium, NF (Amberlite IRP 88) | 6 | 6 | 6.0 |
| 5 | Croscarmellose Sodium, NF | 8 | 8 | 8 |
| 6 | Microcrystalline Cellulose, NF (Avicel PH-101) | 8 | 12 | 8 |
| 7 | Strawberry Flavor (SN302419) | 0.7 | 0.7 | 0.7 |
| 8 | Aspartame Powder, USP (Nutrasweet Powder) | 2.9 | 2.9 | 2.9 |
| 9 | Sodium Stearyl Fumarate, NF | 0.7 | 0.7 | 0.7 |
| 10 | Colloidal Silicon Dioxide, NF (Cab-O-Sil) | 1.1 | 3 | 3 |
| 11 | Magnesium stearate, NF | 0.2 | 0.2 | 0.2 |
|  | Total Tablet Weight | 80 | 80 | 80 |

Figure 10:
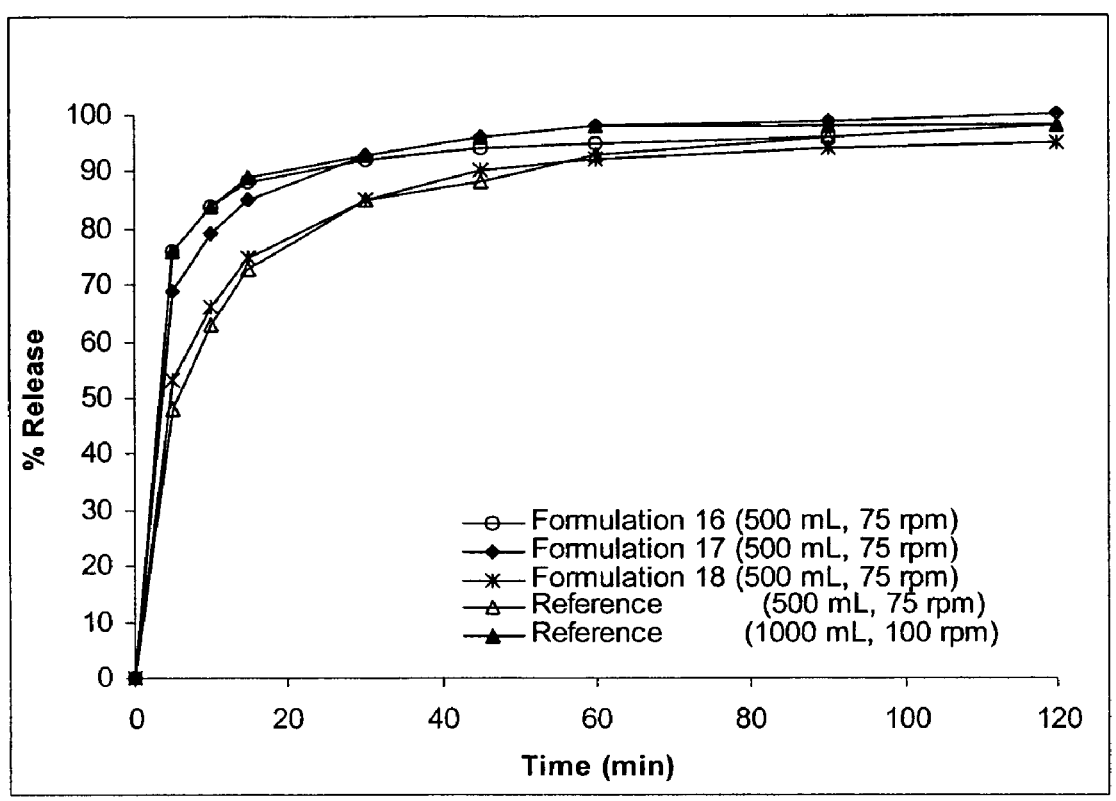
FIG. 10 is a graphical representation comparing the dissolution profiles of Formulation 16 (hollow circle), Formulation 17 (solid diamond), Formulation 18 (solid star), Reference (hollow triangle) and Reference (solid triangle). The dissolution profiles were taken in a medium of 0.1% SDS in 0.1 N HCl with a paddle speed of 75 rpm.

The dissolution profiles of Formulation 16, Formulation 17 and Formulation 18 were taken in a medium of 0.1% SDS (sodium dodecyl sulfate) in 0.1 N HCl. The dissolution profiles of Formulations 16, 17 and 18 as compared to two references (1.5 mg levonorgestrel tablets) are listed in Table 21 and in FIG. 10.

TABLE 21

Dissolution profiles of Formulations 16, 17 and 18 and two references (1.5 mg levonorgestrel tablets).

| Time (min) | Formulation 16 (500 mL, 75 rpm) | Formulation 17 (500 mL, 75 rpm) | Formulation 18 (500 mL, 75 rpm) | Reference (500 mL, 75 rpm) | Reference (1000 mL, 100 rpm) |
|---|---|---|---|---|---|
| 0 | 0 | 0 | 0 | 0 | 0 |
| 5 | 76 | 69 | 53 | 48 | 76 |
| 10 | 84 | 79 | 66 | 63 | 84 |
| 15 | 88 | 85 | 75 | 73 | 89 |
| 30 | 92 | 93 | 85 | 85 | 93 |
| 45 | 94 | 96 | 90 | 88 | 96 |
| 60 | 95 | 98 | 92 | 93 | 98 |
| 90 | 96 | 99 | 94 | 96 | 98 |
| 120 |  | 100 | 95 | 98 | 98 |

Hardness was measured for Formulations 16 and 17. In addition, disintegration times were measured by USP disintegration tester. The hardness and disintegration times of Formulations 16 and 17 are listed in Table 22.

TABLE 22

Comparison of hardness and disintegration times for Formulations 16 and 17 by USP disintegration tester.

| | USP Tester | |
|---|---|---|
| Hardness (kp) | Formulation 16 DT (sec) | Formulation 17 DT (sec) |
| 0.5 | 11 | 6 |
| 1.0 | 9 | 10 |
| 1.5 | 8 | 13 |

TABLE 22-continued

Comparison of hardness and disintegration times for
Formulations 16 and 17 by USP disintegration tester.

| | USP Tester | |
|---|---|---|
| | Formulation 16 | Formulation 17 |
| Hardness (kp) | DT (sec) | |
| 2.0 | 6 | 14 |
| 2.5 | 8 | 15 |

Example 8

The stability of Formulation 16 from Example 7 was tested by quantitative analysis of the compositions. The compositions were initially analyzed immediately after preparing the compositions, and were then placed under accelerated storage conditions for one, two and six weeks at a temperature of 60° C. under air and for 6 weeks at 40° C./75% RH (Relative Humidity). After storage, measurements were made to determine the total amount of levonorgestrel present in each sample (Assay, %) and percent recovery (% Recovery). The results are shown in Table 23.

TABLE 23

Stability data for Formulation 16.
Impurity Summary

| | | Condition | | | | |
|---|---|---|---|---|---|---|
| Name | RRT | Initial % Recovery (Initial) | 60° C. % Recovery (1 wk) | 60° C. % Recovery (2 wk) | 60° C. % Recovery (6 wk) | 40° C./75% RH % Recovery (6 wk) |
| unspecified-1 | 0.337 | ND | 0.01 | ND | ND | 0.05 |
| unspecified-2 | 0.386 | ND | 0.01 | ND | ND | ND |
| 6β | 0.425 | 0.16 | 0.13 | 0.13 | 0.22 | 0.13 |
| 10β | 0.487 | 0.01 | 0.01 | ND | 0.04 | 0.04 |
| unspecified-3 | 0.501 | 0.02 | 0.02 | 0.04 | ND | ND |
| unspecified-4 | 0.539 | 0.02 | 0.02 | 0.02 | 0.02 | 0.02 |
| 6 keto | 0.655 | 0.04 | 0.04 | 0.04 | 0.04 | 0.03 |
| delta 8,14 | 0.869 | 0.06 | 0.06 | 0.06 | 0.06 | 0.06 |
| Levodion | 0.905 | 0.02 | 0.02 | 0.02 | 0.02 | 0.02 |
| unspecified-6 | 0.932 | 0.02 | 0.02 | 0.02 | 0.01 | 0.01 |
| unspecified-7 | 1.197 | ND | 0.01 | 0.01 | ND | ND |
| unspecified-8 | 1.241 | ND | ND | 0.01 | ND | ND |
| Total | | 0.35 | 0.35 | 0.35 | 0.41 | 0.31 |
| ASSAY | | | | | | |
| | | 97.5% | 98.6% | 99.5% | 99.6% | 99.7% |

All of the various embodiments or options described herein can be combined in any and all variations. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A non-effervescent, orally disintegrating solid pharmaceutical dosage form comprising: (a) a progestin equivalent to about 0.5 mg to about 2 mg of levonorgestrel; (b) an ionic disintegrant and no non-ionic disintegrant; and (c) a hydrophilic water-insoluble non-ionic excipient; wherein the ionic disintegrant is present in a concentration of greater than 8% to about 60% by weight of the dosage form and the hydrophilic water-insoluble non-ionic excipient is present in a concentration of about 1% to about 20% by weight of the dosage form.

2. The pharmaceutical dosage form of claim 1, wherein the ionic disintegrant is selected from the group consisting of croscarmellose sodium, sodium starch glycolate, polacrilin potassium, carboxymethyl cellulose calcium and combinations thereof.

3. The pharmaceutical dosage form of claim 1, wherein the ionic disintegrant is croscarmellose sodium.

4. The pharmaceutical dosage form of claim 1, wherein the ionic disintegrant is sodium starch glycolate.

5. The pharmaceutical dosage form of claim 1, wherein the ionic disintegrant is polacrilin potassium.

6. The pharmaceutical dosage form of claim 1, wherein the ionic disintegrant is a combination of croscarmellose sodium and polacrilin potassium.

7. The pharmaceutical dosage form of claim 1, wherein the ionic disintegrant is a combination of sodium starch glycolate and polacrilin potassium.

8. The pharmaceutical dosage form of claim 1, wherein the ionic disintegrant is in a concentration of about 10% to about 50% by weight of the dosage form.

9. The pharmaceutical dosage form of claim 1, wherein the hydrophilic water-insoluble non-ionic excipient is selected from the group consisting of microcrystalline cellulose, pregelatinized starch, cellulose compounds, starches, crospovidone and combinations thereof.

10. The pharmaceutical dosage form of claim 1, wherein the hydrophilic water-insoluble non-ionic excipient is in a concentration of about 2% to about 15% by weight of the dosage form.

11. The pharmaceutical dosage form of claim 1, wherein greater than 40% by weight of the progestin dissolves into solution in less than about 7 minutes when the dosage form is placed in a surfactant containing medium according to USP method II at 75 rpm.

12. The pharmaceutical dosage form of claim 1, wherein at least 75% by weight of the progestin dissolves into solution in less than about 15 minutes when the dosage form is placed in a surfactant containing medium according to USP method II at 75 rpm.

13. The pharmaceutical dosage form of claim 1, wherein at least 75% by weight of the progestin equivalent to about 0.75 mg of levonorgestrel dissolves into solution in less than about 15 minutes when the dosage form is placed in a medium of 5 ppm Tween 80 in 900 mL of water according to USP method II at 75 rpm.

14. The pharmaceutical dosage form of claim 1, wherein at least 75% by weight of the progestin equivalent to about 1.5 mg of levonorgestrel dissolves into solution in less than about 15 minutes when the dosage form is placed in a medium of 0.1% SDS in 0.1 N HC1 according to USP method II at 75 rpm.

15. A method of treating a female in need of emergency contraception, the method comprising: administering post-coitus to the female a first orally disintegrating solid pharmaceutical dosage form; and administering to the female within about 12 hours of administration of the first dosage form a second orally disintegrating solid pharmaceutical dosage form, wherein each of the first and second dosage forms comprises: (a) a progestin equivalent to about 0.75 mg of levonorgestrel; (b) an ionic disintegrant and no non-ionic disintegrant; and (c) a hydrophilic water-insoluble non-ionic excipient; wherein the ionic disintegrant is present in a concentration of greater than 8% to about 60% by weight of the dosage form and the hydrophilic water-insoluble non-ionic excipient is present in a concentration of about 1% to about 20% by weight of the dosage form.

16. A method of treating a female in need of emergency contraception, the method comprising administering postcoitus to the female an orally disintegrating solid pharmaceutical dosage form comprising: (a) a progestin equivalent to about 1.5 mg of levonorgestrel; (b) an ionic disintegrant and no non-ionic disintegrant; and (c) a hydrophilic water-insoluble non-ionic excipient; wherein the ionic disintegrant is present in a concentration of greater than 8% to about 60% by weight of the dosage form and the hydrophilic water-insoluble non-ionic excipient is present in a concentration of about 1% to about 20% by weight of the dosage form.

17. A therapeutic package for treating a female in need of emergency contraception, the package comprising:
(a) one or more non-effervescent, orally disintegrating solid dosage forms of claim 1;
(b) a suitable container; and
(c) a label directing administering the pharmaceutical dosage form to a female in need thereof.

18. A process for preparing a non-effervescent, orally disintegrating solid pharmaceutical dosage form, the process comprising: mixing an ionic disintegrant and no non-ionic disintegrant and a progestin equivalent to about 0.5 mg to about 2 mg of levonorgestrel to form an initial mixture; adding to the initial mixture a hydrophilic water-insoluble non-ionic excipient to form a final mixture; and compressing the final mixture to produce the pharmaceutical dosage form; wherein the ionic disintegrant is present in a concentration of greater than 8% to about 60% by weight of the dosage form and the hydrophilic water-insoluble non-ionic excipient is present in a concentration of about 1% to about 20% by weight of the dosage form.

19. The process of claim 18, wherein the ionic disintegrant is selected from the group consisting of croscarmellose sodium, sodium starch glycolate, polacrilin potassium, carboxymethyl cellulose calcium and combinations thereof.

20. The process of claim 18, wherein the ionic disintegrant is in a concentration of about 10% to about 50% by weight of the dosage form.

21. The process of claim 18, wherein the hydrophilic water-insoluble non-ionic excipient is selected from the group consisting of microcrystalline cellulose, pregelatinized starch, cellulose compounds, starches, crospovidone and combinations thereof.

22. The process of claim 18, wherein the hydrophilic water-insoluble non-ionic excipient is in a concentration of about 2% to about 15% by weight of the dosage form.

23. The process of claim 18, wherein greater than 40% by weight of the progestin dissolves into solution in less than about 7 minutes when the dosage form is placed in a surfactant containing medium according to USP method II at 75 rpm.

24. The process of claim 18, wherein at least 75% by weight of the progestin dissolves into solution in less than about 15 minutes when the dosage form is placed in a surfactant containing medium according to USP method II at 75 rpm.

25. The process of claim 18, wherein at least 75% by weight of the progestin equivalent to about 0.75 mg of levonorgestrel dissolves into solution in less than about 15 minutes when the dosage form is placed in a medium of 5 ppm Tween 80 in 900 mL of water according to USP method II at 75 rpm.

26. The process of claim 18, wherein at least 75% by weight of the progestin equivalent to about 1.5 mg of levonorgestrel dissolves into solution in less than about 15 minutes when the dosage form is placed in a medium of 0.1% SDS in 0.1 N HC1 according to USP method II at 75 rpm.

27. The process of claim 18, further comprising adding a non-polymeric water-soluble carrier to the initial mixture.

28. The process of claim 18, further comprising adding a flavorant, a sweetener or a glidant to the final mixture.

29. The process of claim 18, further comprising adding a lubricant to the final mixture.

* * * * *